United States Patent
Kambe et al.

(10) Patent No.: US 10,556,849 B2
(45) Date of Patent: Feb. 11, 2020

(54) METHOD FOR PRODUCING METHANOL AND APPARATUS FOR PRODUCING METHANOL

(71) Applicant: MITSUBISHI GAS CHEMICAL COMPANY, INC., Tokyo (JP)

(72) Inventors: Yasuaki Kambe, Niigata (JP); Kohei Uchida, Niigata (JP); Takuya Okamura, Niigata (JP); Daigo Hirakawa, Niigata (JP)

(73) Assignee: MITSUBISHI GAS CHEMICAL COMPANY, INC., Tokyo (JP)

(*) Notice: Subject to any disclaimer, the term of this patent is extended or adjusted under 35 U.S.C. 154(b) by 0 days.

(21) Appl. No.: 16/091,309

(22) PCT Filed: Apr. 4, 2017

(86) PCT No.: PCT/JP2017/014078
§ 371 (c)(1),
(2) Date: Oct. 4, 2018

(87) PCT Pub. No.: WO2017/175760
PCT Pub. Date: Oct. 12, 2017

(65) Prior Publication Data
US 2019/0152885 A1 May 23, 2019

(30) Foreign Application Priority Data
Apr. 7, 2016 (JP) ................................. 2016-077448

(51) Int. Cl.
*C07C 29/151* (2006.01)
*B01J 19/00* (2006.01)
(Continued)

(52) U.S. Cl.
CPC ....... *C07C 29/1512* (2013.01); *B01J 19/0013* (2013.01); *B01J 19/2435* (2013.01); *C07C 29/76* (2013.01); *B01J 2219/00074* (2013.01)

(58) Field of Classification Search
CPC ... C07C 29/1512; C07C 29/76; C07C 29/152; C07C 31/04; B01J 19/2435; B01J 19/0013; B01J 2219/0074
See application file for complete search history.

(56) References Cited

U.S. PATENT DOCUMENTS 6,387,963 B1   5/2002  Fitzpatrick
10,252,963 B2 * 4/2019  Kambe ................ B01J 8/0492
(Continued)

FOREIGN PATENT DOCUMENTS

CN    103232321    8/2013
JP    51-10210     4/1976
(Continued)

OTHER PUBLICATIONS

Congming Li et al., "Development of high stable catalyst for methanol synthesis from carbon dioxide", Applied Catalysis A: General, 469, 2014, pp. 306-311.
(Continued)

*Primary Examiner* — Jafar F Parsa
(74) *Attorney, Agent, or Firm* — Greenblum & Bernstein, P.L.C.

(57) ABSTRACT

A method for producing methanol allows the temperature of the catalyst layer to fall within an appropriate temperature range, reduces energy used, and achieves higher carbon yield. In a synthesis loop including at least two synthesis steps and two separation steps, a first mixed gas is obtained by mixing the final unreacted gas with a fraction of the
(Continued)

make-up gas, methanol is synthesized from the first mixed gas after preheating, a first unreacted gas is separated from the obtained first reaction mixture, a final mixed gas is obtained by finally mixing the unreacted gas and a fraction of the make-up gas, the final mixed gas after preheating is further increased in pressure and then methanol is synthesized, a final unreacted gas is separated from the obtained final reaction mixture, and the reaction temperature of the catalyst layer is controlled by the indirect heat exchange with pressurized boiling water.

20 Claims, 5 Drawing Sheets

(51) Int. Cl.
　　　*B01J 19/24*　　　(2006.01)
　　　*C07C 29/76*　　　(2006.01)

(56) References Cited

U.S. PATENT DOCUMENTS

| 2007/0225385 | A1 | 9/2007 | Early |
| 2017/0240492 | A1 | 8/2017 | Kambe et al. |

FOREIGN PATENT DOCUMENTS

| JP | 2005-125244 | 5/2005 |
| JP | 4362013 | 8/2009 |
| WO | 2006/018610 | 2/2006 |
| WO | 2016/063872 | 4/2016 |

OTHER PUBLICATIONS

Masaru Ichikawa et al., "Advanced Utilization Technology of Nattural Gas—Frontier of Development Researches, Chapter 5, Section 2, Methanol Synthesis", NTS, 2001, pp. 446-447.
Official Communication issued in International Bureau of WIPO Patent Application No. PCT/JP2017/014078, dated Jul. 11, 2017.

* cited by examiner

[FIG. 1]
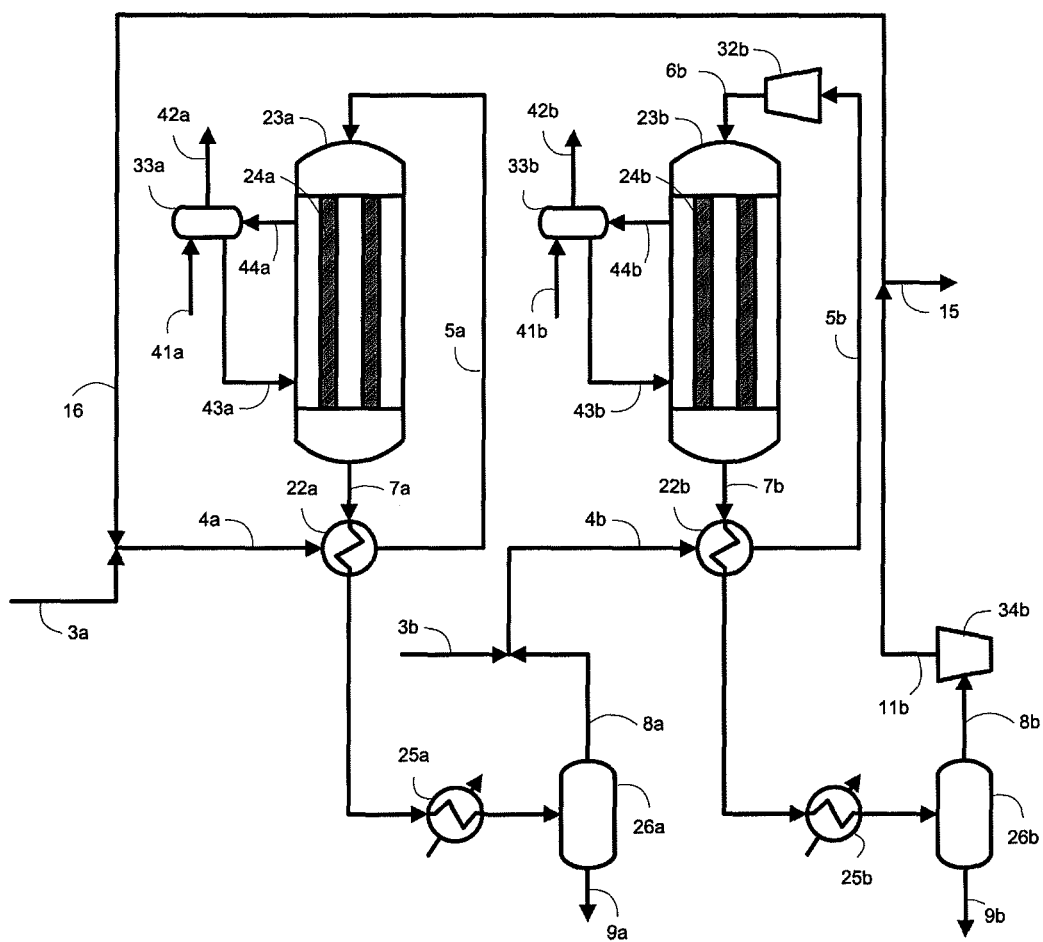

[FIG. 2]
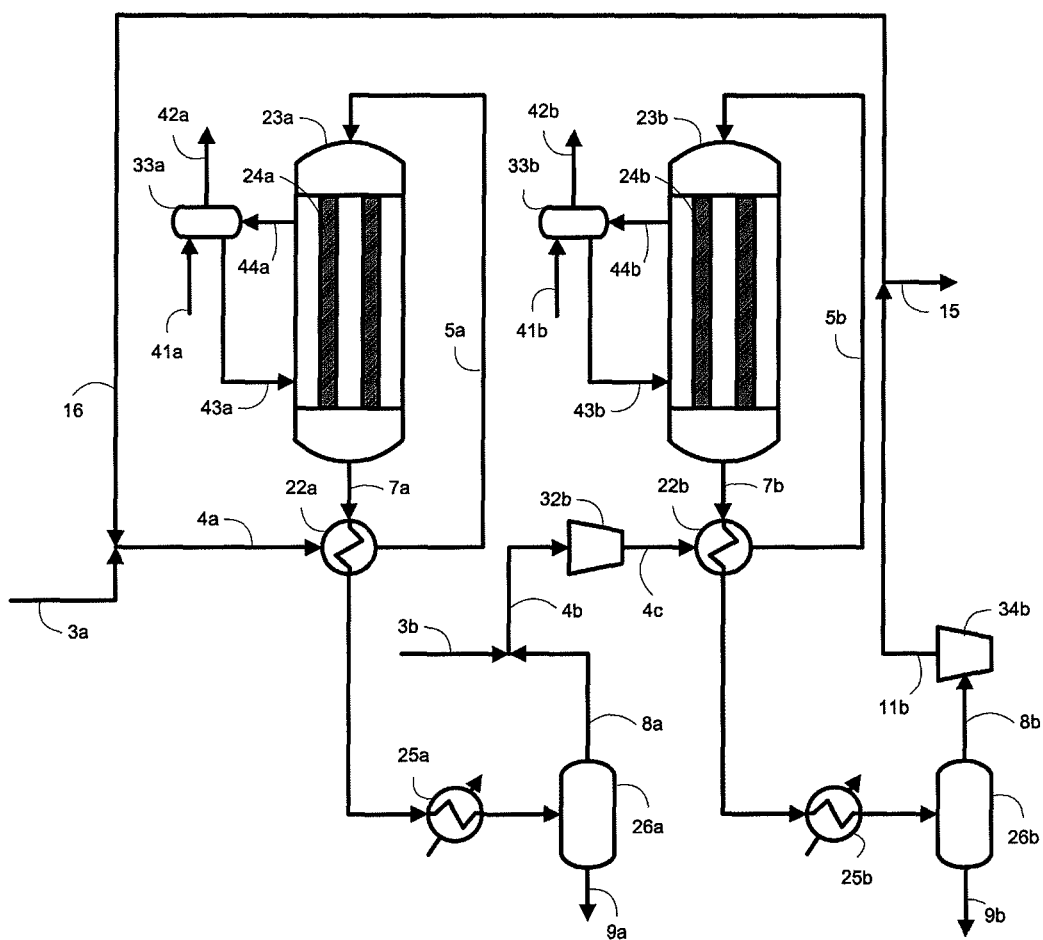

[FIG. 3]
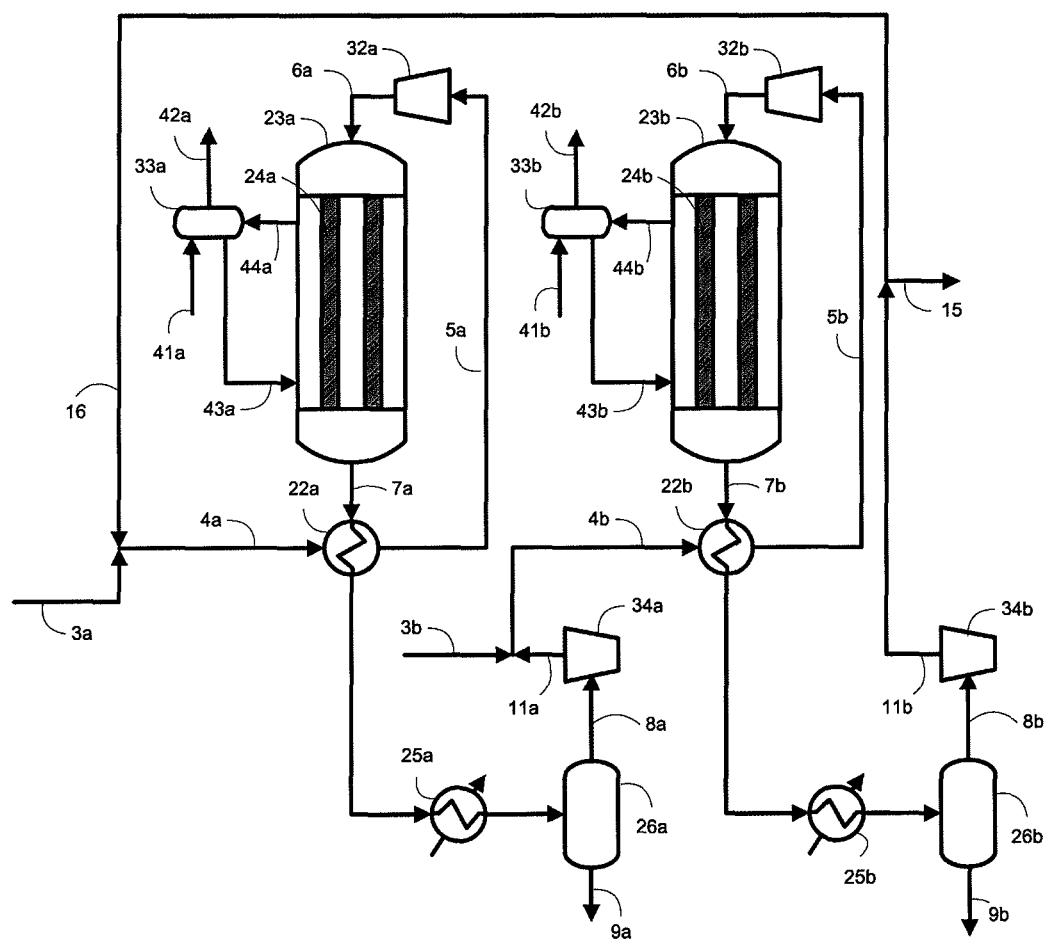

[FIG. 4]
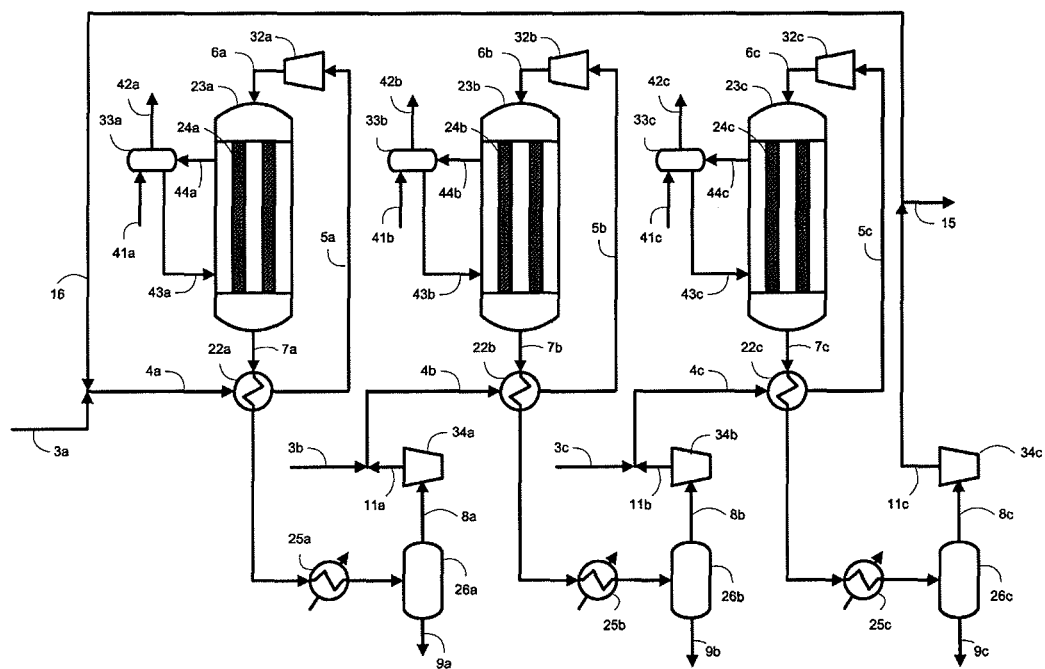

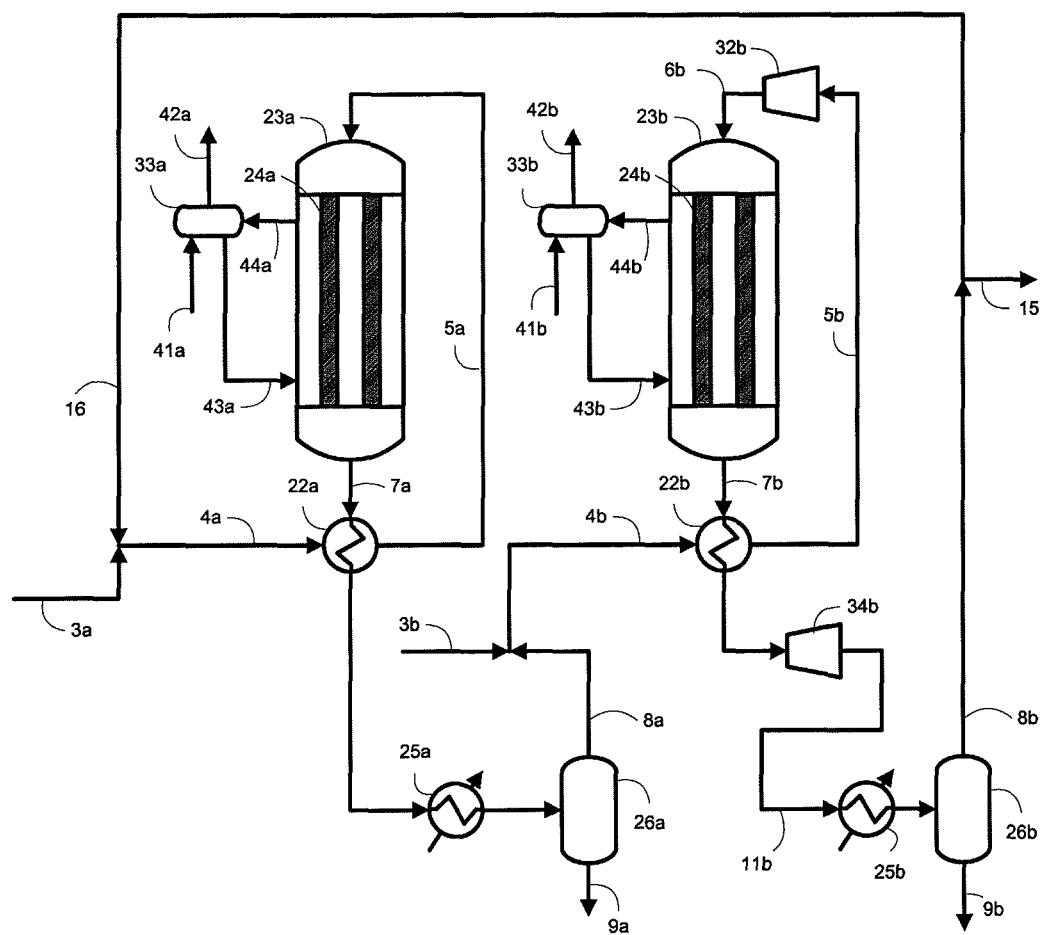
[FIG. 5]

METHOD FOR PRODUCING METHANOL AND APPARATUS FOR PRODUCING METHANOL

TECHNICAL FIELD

The present invention relates to a method for producing methanol and an apparatus for producing methanol.

BACKGROUND ART

Industrial production of methanol is performed by using a fossil fuel as a feedstock, and by allowing a synthesis gas (hereinafter, also referred to as "synthesis raw material gas" or "raw material gas") mainly comprising carbon monoxide, carbon dioxide and hydrogen, obtained by reforming the fossil fuel, to react on a catalyst. The involved reaction conditions are such that the pressure is 50 to 150 kg/cm$^2$, the temperature is 160 to 300° C., and the catalyst used is a catalyst mainly comprising copper/zinc. The methanol synthesis reaction is represented by the following formulas (1) and (2).

[Formula 1]

$$CO + 2H_2 \rightarrow CH_3OH \tag{1}$$

$$CO_2 + 3H_2 \rightarrow CH_3OH + H_2O \tag{2}$$

Patent Document 1 has pointed out a problem that in the methanol synthesis at a low circulation ratio, the reactant partial pressure of the gas is sometimes high, and this causes excessive reaction and the occurrence of overheating of the catalyst bed. Accordingly, Patent Document 1 proposes, in order to solve this problem, that the supplied synthesis raw material gas is divided into two flows, one flow is mixed with the circulation unreacted gas and then introduced into a first synthesis stage, the other flow is mixed with the outlet gas of the first synthesis stage, and before the separation of the synthesized methanol, methanol is synthesized at an additional synthesis stage. The technique disclosed in Patent Document 1 is characterized in that the overheating of a catalyst layer is avoided by regulating the synthesized amount of methanol at the synthesis stage, and at the same time, the circulation ratio represented as the flow rate of the circulation unreacted gas based on the flow rate of the supplied raw material gas can be made as low as 1 to 3.

Patent Document 2 states that the methanol synthesis performed under a low pressure provides an advantage such that the load on a compressor is reduced, or the compressor is made completely unnecessary, but, on the other hand, has a drawback such that a large amount of catalyst is required, or the unreacted gas is required to be recycled at a high circulation ratio. The technique disclosed in Patent Document 2 is characterized in that in order to solve such a drawback, two synthesis reactors are serially installed, and the outlet gas from each of the synthesis reactors is condensed and separated to reduce the circulation ratio so as to be 4.0 or less. Specifically, Examples in Patent Document 2 show that the circulation ratio was altered from 6.0 to 3.5.

Patent Document 3 discloses that higher partial pressures of reactants in reactors can lead to excessive reaction and high temperatures. The document discloses that these high temperatures may lead to a higher deactivation rate for the catalyst. Therefore, Patent Document 3 proposes a technique characterizing in that a plurality of reactors is placed in a synthesis loop; a separator is placed downstream of each of the reactors; the reactant gas can be fed upstream of the reactors and the pressure is increased between the reactors as means for enabling large volumes of the desired product to be produced in an economical manner without a reduction in catalyst life expectancy. Patent Document 3 discloses that the above-described technique enables the production of the desired product to be achieved whilst reducing the circulation rate of gases and controlling the temperatures within the reactors such that an acceptable catalyst life can be achieved. The example of the document indicates that 23% or approximately 28% of the circulation rate of gases is reduced.

When the economic efficiency improvement based on scaling up the plant is pursued, there is generally used a technique to achieve a large scale by parallelizing the points at be bottlenecks. For example, in the process of methanol synthesis, the scale of the plant is sometimes limited by, for example, the production restriction imposed on reactors. In such a case, a plurality of reactors is arranged in parallel to achieve a large scale of the whole plant, as the case may be.

Non Patent Document 1 also discloses the considerable degradation of the catalytic activity caused by the water produced by accompanying the methanol synthesis.

Non Patent Document 2 discloses the course of the development of the methanol synthesis technology. More specifically, the development of the production process of the methanol synthesis technology has been advanced with a focus on the pursuance of the improvement of the energy efficiency and the improvement of the economic efficiency on the basis of the achievement of a large scale of plant. Additionally, according to the description in Non Patent Document 2, as effects accompanying a drastic decrease of the circulating amount of the unreacted gas, the reduction of the electric power used and the cooling water amount used, and the size reduction of the piping in a synthesis loop and peripheral devices such as circulators and heat exchangers are made possible.

CITATION LIST

Patent Documents

Patent Document 1: Japanese Patent No. 4362013
Patent Document 2: Japanese Patent Publication No. 51-10210
Patent Document 3: International Publication No. WO 2006/018610

Non Patent Documents

Non Patent Document 1: Applied Catalysis A: General, 469 (2014), p. 306-311
Non Patent Document 2: Masaaki Kuwa, "Advanced Utilization Technology of Natural Gas—Frontier of Development Researches, Chapter 5, Section 2, Methanol Synthesis," supervised by Masaru Ichikawa, N•T•S, 2001, p. 439, pp. 446 to 447.

SUMMARY OF INVENTION

Technical Problem

The synthesis reaction of methanol is represented by the foregoing formulas (1) and (2), and is known to be a number-of-molecules decrease reaction and a highly exothermic reaction. The currently generally used copper/zinc-based catalyst has an appropriate reaction temperature range from 220 to 280° C., and has a drawback that when the reaction temperature is higher than 280° C., the degradation of the catalyst activity, the decrease of the equilibrium methanol concentration and the increase of the unfavorable side reaction products occur. Accordingly, in order to avoid the overheating of the catalyst, it is necessary to establish at least one of the restriction of the reaction amount occurring in the catalyst layer and the cooling of the catalyst layer.

In addition, the heat generated due to the methanol synthesis promotes the sintering of the catalyst, or as disclosed in Non Patent Document 1, the water produced due to the methanol synthesis promotes the degradation of the catalyst. Therefore, in the methanol synthesis, it is demanded that the load on the catalyst is leveled in effectively using the catalyst, and the catalyst is efficiently used.

Considering the global environment; it is demanded to highly maintain the carbon yield in order to reduce the oxidized carbon amount discarded in the methanol production. In addition, as disclosed in Non Patent Document 2, the drastic decrease of the circulating amount of the unreacted gas, namely, the achievement of a low circulation ratio enables the reduction of the electric power used and the cooling water amount used. Accordingly, in the methanol synthesis process, the achievement of the low circulation ratio is also demanded from the viewpoint of the reduction of the energy used. As described above, Patent Document 1 is characterized in that by dividing the amount of the methanol to be synthesized into a plurality of reactors, while the circulation ratio is being made as low as 1 to 3, the catalyst layer temperature can be maintained appropriately. However, in the methanol synthesis reaction, which is an equilibrium reaction with low conversion rate, there is a problem such that in general, the carbon yield is decreased as the circulation ratio is made lower. Actually, when the carbon yield in the methanol synthesis reaction is calculated from the results of Example 2 disclosed in Patent Document 1, the carbon yield is found to be 76.2%, so as to be decreased as compared with Example 1 serving as a comparative example, and thus Example 2 is not practical. Here, the carbon yield is represented by the ratio of the methanol molar flow rate in the crude methanol to the oxidized carbon gases (carbon monoxide and carbon dioxide) molar flow rate in the make-up gas. Patent Document 1 also presents Example 3 as an example of a technique to improve the carbon yield by installing an apparatus which allows a purge gas to further react. However, the installation of an additional reaction apparatus and the units to be attached thereto requires a large scale of facility investment. In addition, in Patent Document 1, as can be seen from the scope of claims and the accompanying drawings, there is no technical idea such that the unreacted gas is separated from the outlet gas of the first synthesis stage, and the unreacted gas is used as a raw material for the next synthesis stage. Instead, in the scope of claims and the accompanying drawings of Patent Document 1, the outlet gas in the first synthesis stage is disclosed to be wholly fed to the second synthesis stage, so as to exclude the above-described technical idea.

Moreover, Patent Document 2 states that a synthesis under low pressure and with a low circulation ratio has been made possible by condensation separation of products including methanol between synthesis reactors. However, in Examples of Patent Document 1, the circulation ratio was altered from 6.0 to 3.5, not to lead to improvement of the carbon yield. When in such a process as disclosed in Patent Document 2, with the intention of improving the yield and reducing the amount of energy used, (1) the synthesis pressure is increased, (2) the catalyst activity is improved, or (3) the circulation ratio is further reduced, unpreferably the deviations of the methanol production amounts of the respective synthesis reactors tend to be augmented, and at the same time, the deviations of the loads on the catalysts also tend to be augmented. When the deviations of the loads on the catalysts are augmented, the differences are caused among the catalyst degradations. Accordingly, when the catalysts are intended to be replaced at the same time, the catalysts used in some synthesis reactors are replaced under the conditions that the service lives of the catalysts are not yet expired. In other words, when the respective catalysts are intended to be replaced when the catalysts reach the desired service lives thereof, the catalyst replacement timings of the respective synthesis reactors are largely different from each other. Consequently, the efficiency of the operations in the methanol production is degraded.

Patent Document 3 discloses that the above-described technique enables the production of the desired product to be achieved whilst reducing the circulation rate of gases and controlling the temperatures within the reactors such that an acceptable catalyst life can be achieved. However, the example of the document only indicates that the circulation rate of gases can be reduced only to 72% or 77% of the prior art, and fails to disclose the carbon yield. Unless considering the carbon yield, the increase of the reactant gas can maintain the methanol production amounts even if the circulation rate of the gases is reduced. Accordingly, the technique disclosed in Patent Document 3 has no innovation.

Furthermore, it is the most favorable for the carbon yield to provide the outlet of the purge gas at the farthest position from the inlet of the make-up gas within the synthesis loop. On the contrary, it is favorable, from the viewpoint of the amount of the gas throughput at the circulator, to arrange the splitting point of the purge gas at just upstream of the circulator within the synthesis loop. The process disclosed in Patent Document 3 increases the pressure of the gas, i.e., the gas discharged from the synthesis loop, which is unnecessary to be pressurized. Such process is not appropriate since the amount of the gas throughput at the circulator is increased and such increase results in the increase of the energy used.

In addition, when the outlet temperature of a cooler, which is not a water cooling heat exchanger but an air fin cooler for the purpose of the reduction of cooling water or the equipment cost, is adjusted to a range from 55° C. to 90° C. to reduce the separation proportion of methanol in a condensation separation step except for the final condensation separation step, the total amount of a condensable gas introduced to a circulator is increased if the circulator is placed downstream of the equipment used in the condensation separation step. Such case is associated with a high probability of generating a condensate liquid in the circulator. The placement of the circulator is not appropriate since the generation of the condensate liquid causes mechanical trouble and energy loss.

Moreover, as disclosed in Non Patent Document 2, in general, the improvement of the methanol synthesis technology as viewed from the aspect of production process has been performed with a focus on the pursuance of the improvement of the energy efficiency and the improvement of the economic efficiency on the basis of the achievement of a large scale of plant. For example, according to Patent Document 1, an object is to increase the methanol production, and it can be seen that the improvement of economic efficiency is demanded. As viewed from such a trend of the improvement of the methanol synthesis technology, the condensation separation of the products between the synthesis stages as disclosed in Patent Document 2 results in the discharge of a large fraction of energy into the environment, so as to go against the current trend. Specifically, in Examples disclosed in Patent Document 2, the circulation gas amount is 3.5 times the raw material gas amount, and the gas amount flowing while being cooled from the outlet of the first synthesis reactor to a separator is 3.5 or more times the raw material gas amount. Accordingly, unpreferably a large amount of gas is required to be cooled, so as to increase the load on the cooler.

With respect to the parallelization performed when the improvement of the economic efficiency is pursued on the basis of the achievement of a large scale of plant, the achievement of a large scale of plant is made possible in the case where the reactors are parallelized because of the increase of the gas amount capable of being introduced into the reactors. However, in general, such a parallelization does not lead to the yield improvement or the reduction of the circulation ratio.

The present invention has been achieved in view of at least part of such circumstances as described above, and the technical problem of the present invention is to provide a method for producing methanol and an apparatus for producing methanol in each of which in the synthesis of methanol, the temperature of the catalyst layer is allowed to fall within an appropriate temperature range, the amount of energy used is reduced, and moreover a high carbon yield is achieved.

Solution to Problem

The present inventors made a diligent study in order to solve the above-described problems. Consequently, the present inventors have perfected the present invention by discovering that by adopting a specific process, the suppression of the catalyst overheating is achieved, and at the same time, it is possible to jointly achieve the improvement of the yield and the reduction of the amount of energy used. The specific process has a plurality of methanol synthesis steps, and the unreacted gas separated from the reaction mixture produced in a methanol synthesis step is introduced into the successive methanol synthesis step. Moreover, the final unreacted gas separated from the reaction mixture produced in the methanol synthesis step in the final stage, removed partially as a purge gas, and mixed with a portion of the make-up gas is introduced into the first methanol synthesis step, and thus there is formed a synthesis loop allowing the unreacted gas to pass serially through the respective reactors. In addition, the raw material gas is divided to be introduced, at positions in advance of the respective reactors, into the synthesis loop. Additionally, the synthesis loop has a step of preheating and subsequently increasing in pressure the supplied gas in the methanol synthesis step in the final stage. Specifically, the present invention is as follows.

[1] A method for producing methanol comprising: synthesis steps of synthesizing methanol from a synthesis gas including hydrogen, carbon monoxide and carbon dioxide; and separation steps of separating an unreacted gas from a reaction mixture obtained by passing through one of the synthesis steps, the method including a synthesis loop having at least two of the synthesis steps and at least two of the separation steps, wherein the synthesis loop includes: a first mixing step of obtaining a first mixed gas by mixing a residual gas, obtained by removing a purge gas from a final unreacted gas separated from a final reaction mixture in a final separation step subsequent to a final synthesis step, with 10 to 90 mol % of a make-up gas including hydrogen, carbon monoxide and carbon dioxide; a first synthesis step of synthesizing methanol from the first mixed gas; a first separation step of separating a first unreacted gas from a first reaction mixture obtained in the first synthesis step; a final mixing step of obtaining a final mixed gas by finally mixing the unreacted gas and at least a fraction of 10 to 90 mol % of the make-up gas; the final synthesis step of synthesizing methanol from the final mixed gas; and the final separation step of separating the final unreacted gas from the final reaction mixture obtained in the final synthesis step, the synthesis loop also includes: a first preheating step of preheating the first mixed gas; a final preheating step of preheating the final mixed gas; and a pressure increase step of increasing the pressure of the final mixed gas having passed through the final preheating step before the final synthesis step by using a circulator, and in the synthesis loop, a reaction temperatures of a catalyst layer is controlled by indirect heat exchange with pressurized boiling water.

[2] The method for producing methanol according to [1], wherein a heat source for preheating the final mixed gas in the final preheating step is the final reaction mixture.

[3] The method for producing methanol according to [2], further comprising a final reaction mixture pressure reduction step of reducing the pressure of the final reaction mixture having preheated the final mixed gas before the final separation step.

[4] The method for producing methanol according to any one of [1] to [3], further comprising a final unreacted gas pressure reduction step of reducing the pressure of the final unreacted gas obtained in the final separation step before the first mixing step.

[5] The method for producing methanol according to any one of [1] to [4], further comprising a pressure increase step of increasing the pressure of the first mixed gas having passed through the first preheating step before the first synthesis step.

[6] The method for producing methanol according to any one of [1] to [5], wherein a heat source for preheating the first mixed gas in the first preheating step is the first reaction mixture.

[7] The method for producing methanol according to [6], further comprising a first reaction mixture pressure reduction step of reducing the pressure of the first reaction mixture having preheated the first mixed gas before the first separation step.

[8] The method for producing methanol according to any one of [1] to [7], further comprising a first unreacted gas pressure reduction step of reducing the pressure of the first unreacted gas obtained in the first separation step.

[9] The method for producing methanol according to any one of [1] to [8], wherein the pressure ratio between before and after the pressure increase in the pressure increase step exceeds 1.10.

[10] The method for producing methanol according to any one of [1] to [9], further comprising an intermediate mixing step of obtaining an intermediate mixed gas by mixing an unreacted gas and at least a fraction of 10 to 90 mol % of the make-up gas subsequently to the first separation step and before the final mixing step; an intermediate synthesis step of synthesizing methanol from the intermediate mixed gas; and an intermediate separation step of separating an intermediate unreacted gas from the intermediate reaction mixture obtained in the intermediate synthesis step.

[11] The method for producing methanol according to any one of [3], [4], [7] and [8], wherein energy is collected in at least one step of the pressure reduction steps.

[12] An apparatus for producing methanol comprising: reactors for synthesizing methanol from a synthesis gas including hydrogen, carbon monoxide and carbon dioxide; and separators for separating the unreacted gas from the reaction mixture obtained in one of the reactors, the apparatus including a synthesis loop including at least two of the reactors and at least two of the separators, wherein the synthesis loop includes: a first mixing unit for obtaining a first mixed gas by mixing a residual gas, obtained by removing a purge gas from a final unreacted gas separated from a final reaction mixture in a final separator subsequent to a final reactor, with 10 to 90 mol % of a make-up gas including hydrogen, carbon monoxide and carbon dioxide; a first reactor for synthesizing methanol from the first mixed gas; a first separator for separating a first unreacted gas from the first reaction mixture obtained in the first reactor; a final mixing unit for obtaining a final mixed gas by finally mixing the unreacted gas and at least a fraction of 10 to 90 mol % of the make-up gas; the final reactor for synthesizing methanol from the final mixed gas; and the final separator for separating the final unreacted gas from the final reaction mixture obtained in the final reactor, the synthesis loop also includes: a first preheater for preheating the first mixed gas; a final preheater for preheating the final mixed gas; and a circulator for increasing the pressure of the final mixed gas preheated by the final preheater before the preheated final mixed gas is supplied to the final reactor, and at least in the final reactor, a reaction temperature of a catalyst layer is controlled by indirect heat exchange with pressurized boiling water.

Advantageous Effects of Invention

According to the present invention, it is possible to provide a method for producing methanol and an apparatus for producing methanol in each of which in the synthesis of methanol, the temperature of the catalyst layer is allowed to fall within an appropriate temperature range, the amount of energy used is reduced, and moreover a high carbon yield is achieved.

BRIEF DESCRIPTION OF DRAWINGS

FIG. 1 is a schematic diagram illustrating an example of the production apparatus used for the method for producing methanol of the present invention;

FIG. 2 is a schematic diagram illustrating an example of the production apparatus used for the method for producing methanol corresponding to a Comparative Example;

FIG. 3 is a schematic diagram illustrating another example of the production apparatus used for the method for producing methanol of the present invention;

FIG. 4 is a schematic diagram illustrating yet another example of the production apparatus used for the method for producing methanol of the present invention; and FIG. 5 is a schematic diagram illustrating still yet another example of the production apparatus used for the method for producing methanol of the present invention.

DESCRIPTION OF EMBODIMENTS

Hereinafter, the mode for carrying out the present invention (hereinafter, simply referred to as the present embodiment) is described in detail with reference to the accompanying drawings if necessary, but the present invention is not limited to the following present embodiment. The present invention can be modified in various ways within the scope not departing from the gist of the present invention. In the accompanying drawings, the same elements will be denoted by the same symbols, and the duplicated descriptions will be omitted. The positional relations such as up, down, left and right are based on the positional relations shown in the drawings, unless otherwise specified. Moreover, the dimensional proportions in the drawings are not limited to the proportions shown in the drawings.

The method for producing methanol of the present embodiment is a method for producing methanol including: a synthesis step of synthesizing methanol from a synthesis gas including hydrogen, carbon monoxide and carbon dioxide; and a separation step of separating an unreacted gas from a reaction mixture obtained by passing through the synthesis step, the method including a synthesis loop having at least two synthesis steps and at least two separation steps, wherein the synthesis loop includes: a first mixing step of obtaining a first mixed gas by mixing a residual gas, obtained by removing a purge gas from a final unreacted gas separated from a final reaction mixture in a final separation step subsequent to a final synthesis step, with 10 to 90 mol % of a make-up gas including hydrogen, carbon monoxide and carbon dioxide; a first synthesis step of synthesizing methanol from the first mixed gas; a first separation step of separating a first unreacted gas from the first reaction mixture obtained in the first synthesis step; a final mixing step of obtaining a final mixed gas by finally mixing the unreacted gas and at least a fraction of 10 to 90 mol % of the make-up gas; the final synthesis step of synthesizing methanol from the final mixed gas;

and a final separation step of separating the final unreacted gas from the final reaction mixture obtained in the final synthesis step, the synthesis loop also includes: a first preheating step of preheating the first mixed gas; a final preheating step of preheating the final mixed gas; and a pressure increase step of increasing the pressure of the final mixed gas having passed through the final preheating step before the final synthesis step by using the circulator, and in the synthesis loop, the reaction temperature of a catalyst layer is controlled by indirect heat exchange with pressurized boiling water. When the heat source for preheating the first mixed gas is the first reaction mixture, the first reaction mixture is cooled by the first mixed gas, and accordingly is more easily condensed. Similarly, when the heat source for preheating the final mixed gas is the final reaction mixture, the final reaction mixture is cooled by the final mixed gas, and accordingly is more easily condensed.

The apparatus for producing methanol of the present embodiment is an apparatus used for the above-described method for producing methanol. More specifically, the apparatus for producing methanol of the present embodiment is an apparatus for producing methanol including: a reactor synthesizing methanol from a synthesis gas including hydrogen, carbon monoxide and carbon dioxide; and a separator separating the unreacted gas from the reaction mixture obtained in the reactor, the apparatus including a synthesis loop including at least two reactors and at least two separators, wherein the synthesis loop includes: a first mixing unit obtaining a first mixed gas by mixing a residual gas, obtained by removing a purge gas from a final unreacted gas separated from a final reaction mixture in a final separator subsequent to a final reactor, with 10 to 90 mol %, preferably 10 to 70 mol % of a make-up gas including hydrogen, carbon monoxide and carbon dioxide; a first reactor synthesizing methanol from the first mixed gas; a first separator separating a first unreacted gas from the first reaction mixture obtained in the first reactor; a final mixing unit obtaining a final mixed gas by finally mixing the unreacted gas and at least a fraction of 10 to 90 mol %, preferably 30 to 90 mol % of the make-up gas; the final reactor synthesizing methanol from the final mixed gas; and the final separator separating the final unreacted gas from the final reaction mixture obtained in the final reactor, the synthesis loop also includes: a first preheater for preheating the first mixed gas; a final preheater for preheating the final mixed gas; and a circulator for increasing the pressure of the final mixed gas preheated by the final preheater before the preheated final mixed gas is supplied to the final reactor, and at least in the final reactor, the reaction temperature of a catalyst layer is controlled by indirect heat exchange with pressurized boiling water.

In the present embodiment, at least one separation step is disposed in the fore stage of the final synthesis step. In the present embodiment, in at least one separation step other than the final separation step, the reaction product including methanol and the unreacted synthesis gas (hereinafter, referred to as the "unreacted gas") are separated from the reaction mixture obtained in the immediately preceding synthesis step, and methanol is synthesized in the synthesis step in the subsequent stage from the mixed gas obtained by mixing the unreacted gas with the make-up gas.

(Synthesis Loop)

In the present embodiment, the synthesis loop is formed in the following way: the gas passing through at least one synthesis step and at least one separation step passes through the final synthesis step and the final separation step, and the unreacted gas separated in the final separation step is used as the raw material gas in the first synthesis step. In order to circulate the gas in the synthesis loop, the apparatus for producing methanol comprises at least a circulator for increasing the pressure, and the pressure increase step is arranged after the final preheating step and before the final synthesis step. In this way, it is possible to reduce the energy for increasing the reaction temperature in the final synthesis step, and it is possible to increase the amount of collected heat in the reactor in the step concerned. The temperature increase is made possible by the pressure increase in the pressure increase step, and accordingly it is possible to decrease the temperature required during the preheating of the final mixed gas in advance of pressure increase step. In that case, the temperature difference between the fluid on the lower temperature side and the fluid on the higher temperature side in the preheater used for preheating becomes large, and hence it is possible to increase the heat exchange amount (the amount of collected heat) in the preheater or to reduce the size of the heat exchanger. It is preferable to introduce a high dryness fluid into the circulator. More specifically, it is preferable to increase the dryness by preheating after the separation step a fluid having the condensable gas in the saturation state, to increase the dryness by mixing a high dryness fluid (for example, the make-up gas), or to perform both of these operations. In this way, it is possible to suppress the generation of the condensed droplets in the circulator, and hence it is possible to further prevent the mechanical failure or the increase of energy loss.

Moreover, the synthesis loop may have a pressure reduction step. The pressure reduction step is preferably a step of reducing the pressure before the unreacted gas is subsequently mixed with the make-up gas. More specifically, the pressure reduction step is preferably a final unreacted gas pressure reduction step of reducing the pressure of the final unreacted gas obtained in the final separation step before the first mixing step. In this way, it is possible to increase the pressure in the final separation step in the fore stage of the pressure reduction step, and hence it is possible to further improve the gas-liquid separation efficiency in the final separation step. Similarly, the pressure reduction step is also preferably a first unreacted gas pressure reduction step of reducing the pressure of the first unreacted gas obtained in the first separation step. Instead of or in addition to such a pressure reduction step, the pressure reduction step is preferably a pressure reduction step of reducing the pressure of the reaction mixture before the separation step. When the heat source for preheating the mixed gas is the reaction mixture thereof, it is preferable to reduce the pressure of the reaction mixture after preheating the mixed gas. More specifically, the pressure reduction step is preferably a final reaction mixture pressure reduction step of reducing the pressure of the final reaction mixture having preheated the final mixed gas, before the final separation step, or alternatively preferably a first reaction mixture pressure reduction step of reducing the pressure of the first reaction mixture, namely, the first reaction mixture having preheated the first mixed gas, before the first separation step. Thus, because the fluid can be cooled in the pressure reduction step, it is possible to reduce the size of or to render unnecessary the condenser used for condensing a fraction of the reaction mixture before the separation step.

As the material entering of the material entering into and exiting from the synthesis loop, the make-up gas is divided into a plurality of flows, and then the plurality of flows is introduced into the synthesis loop from the mixing steps in advance of the respective synthesis steps. As the material exiting of the material entering and exiting, the reaction product in the reaction mixture is separated in the separation step and extracted to outside the synthesis loop, and the purge gas is taken out to outside the synthesis loop in order to prevent the accumulation of inert components. In the present specification, the "reaction mixture" is the outlet component of the synthesis step, namely, a mixture including the component produced from the reaction in the synthesis step and the unreacted component, and usually includes methanol.

The unreacted gas in each of the separation steps is introduced into the subsequent mixing step, synthesis step and separation step, and the respective unreacted gases form the synthesis loop, capable of being serially introduced into all the reactors.

The final synthesis step is not particularly limited, and can be any step that synthesizes methanol from the mixed gas obtained by mixing the unreacted gas and the make-up gas, the unreacted gas being separated from the reaction mixture passing through the synthesis steps synthesizing methanol subsequently to the first synthesis step. The final synthesis step is preferably a step (the second synthesis step) of synthesizing methanol from the second mixed gas. Alternatively, the final synthesis step is also preferably a step (the third synthesis step) of synthesizing methanol from the third mixed gas obtained by mixing the second unreacted gas and the make-up gas, the second unreacted gas being separated from the second reaction mixture obtained in the second synthesis step. Of the second synthesis step and the third synthesis step, the final synthesis step is more preferably the second synthesis step.

The final separation step is not particularly limited, and can be any step that separates the unreacted gas from the reaction mixture subsequently to the first separation step. The final separation step is preferably the second separation step of separating the second unreacted gas from the second reaction mixture obtained in the second synthesis step. Alternatively, the final separation step is preferably the third separation step of separating the third unreacted gas from the third reaction mixture obtained in the third synthesis step. Of the second separation step and the third separation step, the final separation step is more preferably the second separation step.

(Make-Up Gas)

The make-up gas is a gas obtained by increasing the pressure of a synthesis raw material gas including carbon monoxide (CO), carbon dioxide ($CO_2$) and hydrogen ($H_2$) such as a steam reformed gas of natural gas or coal gasification gas, to the reaction pressure by using a compressor. The reaction pressure may be, for example, 4.9 to 14.7 MPa-G (50 to 150 kg/cm$^2$-G), is more preferably 7.8 to 10.8 MPa-G (80 to 110 kg/cm$^2$-G). Industrially, the make-up gas is obtained, for example, by the steam-reforming reaction using natural gas as a raw material, and the relation (M) among the mol % values of CO, $CO_2$ and $H_2$ derived from the following formula is preferably larger than 1.0 and 2.0 or less, and more preferably 1.3 to 1.5:

$$M=(H_2 \text{ mol \%})/(2 \times CO \text{ mol \%} + 3 \times CO_2 \text{ mol \%})$$

(Division of Make-Up Gas)

In the present embodiment, the make-up gas is divided into a plurality of flows before being introduced into the synthesis loop, and introduced into the synthesis loop as a fraction of the raw material gas in the plurality of synthesis steps present in the synthesis loop. The preferable ranges of the division proportions of the make-up gas are different depending on the synthesis conditions in the respective synthesis steps and the separation conditions in the respective separation steps. However, the molar flow rate of the make-up gas included in the mixed gas (the first mixed gas) supplied to the first methanol synthesis step (the first synthesis step) is 10 to 90 mol %, preferably 10 to 70 mol % based on the total amount of the make-up gas. Next, the molar flow rate of the make-up gas included in the mixed gas (the second mixed gas) supplied to the second synthesis step is 10 to 90 mol %, preferably 10 to 70 mol % based on the total amount of the make-up gas. In a case where the third and later synthesis steps are present and the total molar flow rates of the make-up gas supplied to the first synthesis step and the second synthesis step is set at less than 100% of the total amount of the make-up gas, the residual make-up gas is appropriately divided to be supplied to the respective third or later methanol synthesis steps. In addition, even if the third and later synthesis steps are present and the total molar flow rates of the make-up gas supplied to the first synthesis step and the second synthesis step is set at 100% of the total amount of the make-up gas, the make-up gas is not divided to the respective third and later methanol synthesis steps. For example, as an embodiment, here is described a case of a production method using a condensation separation method as the separation method in the separation step and having two synthesis steps and two condensation separation steps. In this embodiment, in a case where the temperature of the outlet gas of the first condensation separation step is set at 20° C. to 100° C., the proportion of the make-up gas (the proportion based on the total amount of the make-up gas; the same also applies hereinafter) introduced into the synthesis loop immediately in advance of the final synthesis step (the second synthesis step) is preferably 10 to 90 mol %, more preferably 30 to 90 mol % and further preferably 40 to 70 mol %, for example, from the viewpoint of the carbon yield and the highest temperature of the catalyst layer. In addition, in a case where the temperature of the outlet gas of the first condensation separation step is set at 40° C. to 80° C., the proportion of the make-up gas introduced into the synthesis loop immediately in advance of the final synthesis step may be 10 to 90 mol %, and is preferably 30 to 90 mol %, more preferably 40 to 70 mol % and furthermore preferably 45 to 65 mol % from the same viewpoint as described above.

The synthesis gas serving as the raw material gas for the synthesis step is supplied to the synthesis step after being preferably heated to 180 to 260° C. with a preheater. The synthesis gas temperature when supplied to the synthesis step is appropriately set according to, for example, the type and amount of the catalyst, the type of the reactor and the reaction pressure, and the preferable synthesis gas temperature is 200 to 250° C. From the viewpoint of the energy collection in the reactor, the more preferable gas temperature at the reactor inlet is a temperature higher than the temperature of the pressurized boiling water used for cooling the catalyst layer.

The proportion (division proportion) of the make-up gas mixed in the unreacted gas in the mixing step is preferably regulated according to the desired temperatures of the respective reactors in the synthesis step. The desired temperatures as referred to herein mean the temperatures in the methanol synthesis reaction described later.

In the present embodiment, the make-up gas is divided into a plurality of flows before the make-up gas is introduced into the synthesis loop, and the division proportions of the of flows can be adjusted. Accordingly, the temperatures of the reactors in the synthesis steps can be easily controlled.

(Synthesis Step and Catalyst)

In the synthesis step, methanol is synthesized from the synthesis gas. The reactor used in the synthesis step preferably includes, in addition to a catalyst layer, a mechanism (heat-removing mechanism) for removing the heat produced by the reaction from the catalyst layer.

The catalyst used in the synthesis is preferably a methanol synthesis catalyst including copper atoms and zinc atoms as the essential components. Such a catalyst is reduced from the state of oxide by a reducing gas such as hydrogen or carbon monoxide, or a mixed gas including hydrogen and carbon monoxide, and consequently the copper is activated to give catalytic activity to the catalyst. The catalyst may also include, in addition to the copper atoms and the zinc atoms, aluminum atoms and/or chromium atoms as the main third component. The catalyst including copper and zinc as the essential components can be prepared by heretofore known methods. Such a catalyst can be prepared by the methods disclosed in, for example, Japanese Patent Publication No. 51-44715, Japanese Patent No. 2695663, Japanese Patent Publication No. 06-35401, Japanese Patent Application Laid-Open No. 10-272361, and Japanese Patent Application Laid-Open No. 2001-205089.

A preferable catalyst is a methanol synthesis catalyst including the copper atoms and the zinc atoms in an atomic ratio (copper/zinc) of 2.0 to 3.0, and additionally aluminum atoms. Examples of such a catalyst include the catalysts prepared by the method disclosed in Japanese Patent Application Laid-Open No. 08-299796, and the catalyst disclosed in International Publication No. WO 2011/048976.

Examples of a preferable catalyst include the catalysts used in Examples and Comparative Examples such as Example 2 and Example 3 in International Publication No. 2011/048976. The more preferable atomic ratio (copper/zinc) of the copper atoms and the zinc atoms in the catalyst falls within a range from 2.1 to 3.0. The methanol synthesis catalyst additionally including alumina in a content of 3 to 20% by mass is furthermore preferable. As described above, such a catalyst can be prepared by, for example, the method disclosed in International Publication No. 2011/048976. More specifically, such a catalyst is prepared by, for example, a production method including: a step of producing a precipitate including copper and zinc by mixing an aqueous solution containing copper and an aqueous solution containing zinc and an alkaline aqueous solution; a step of obtaining a mixture by mixing the obtained precipitate and an alumina hydrate having a pseudo boehmite structure; and a step of molding the obtained mixture so as to have a density of 2.0 to 3.0 g/mL. However, the catalyst used in the present embodiment is not limited to the above-described catalyst and the catalyst prepared by the above-described preparation method, and may also be other catalysts having the equivalent methanol synthesis activity.

The method for removing heat from the catalyst layer is preferably a method for indirectly exchanging heat between the catalyst layer and pressurized boiling water by using pressurized boiling water as a coolant. Here, the pressurized boiling water means the water boiling so as to utilize the latent heat in the removal of heat from the catalyst layer. Examples of the heat-removing mechanism related to such a heat-removing method include: a cooling mechanism allowing pressurized boiling water to flow in a counter-flow direction or a co-current flow direction in relation to the gas flow direction in the catalyst layer; and a cooling mechanism allowing pressurized boiling water to flow in a direction perpendicular to the gas flow direction in the catalyst layer. More specifically, examples of the above-described heat-removing mechanism include: a multitubular reactor having an inner tubes parallel to the gas flow direction of the catalyst layer, forming a catalyst layer on the inside of the inner tubes and allowing a coolant to flow on the outside of the inner tubes; the multitubular reactor having the inner tubes parallel to the gas flow direction of the catalyst layer, forming the catalyst layer on the outside of the inner tubes, and allowing the coolant to flow on the inside of the inner tubes; and an interlayer cooling reactor allowing the coolant to flow in the inner tubes disposed so as to be perpendicular to the gas flow direction of the catalyst layer. The temperature of the pressurized boiling water serving as the coolant is preferably 210 to 260° C. The use of the steam produced from the pressurized boiling water is preferably the use as the raw material steam for the steam-reforming reaction of the natural gas. In this case, the pressure of the pressurized boiling water preferably has a pressure higher than the pressure (1.5 to 2.5 MPa-G (15 to 25 kg/cm$^2$-G)) of the common steam-reforming reaction, and hence the temperature of the pressurized boiling water is more preferably, for example, 220 to 240° C.

The control of the reaction temperature of the catalyst layer by the indirect heat exchange with the pressurized boiling water may be performed at least in the final synthesis step; however, it is preferable to control the reaction temperature of the catalyst layer by the indirect heat exchange with the pressurized boiling water in all the synthesis steps. When the pressurized boiling water is used as the coolant in a plurality of reactors, the temperatures of the pressurized boiling water in the respective reactors may be the same as each other or may be different from each other.

The methanol synthesis reaction in the synthesis step is, as is well known, preferably performed under the conditions that the pressure is 4.9 to 14.7 MPa-G (50 to 150 kg/cm$^2$-G) and the temperature is 200 to 300° C. The pressure and the temperature in the methanol synthesis reaction are more preferably 7.8 to 10.8 MPa-G (80 to 110 kg/cm$^2$-G) and 200 to 280° C., respectively, and furthermore preferably 7.8 to 10.8 MPa-G (80 to 110 kg/cm$^2$-G) and 200 to 270° C., respectively.

When a plurality of reactors has the same catalyst amount, the ratio of the maximum amount to the minimum amount of the methanol production amounts in the respective methanol synthesis steps is preferably 1 to 3 and more preferably 1 to 2.

(Separation Step)

In the separation step, the unreacted gas is separated from the reaction mixture including the reaction product obtained in the synthesis step. In other words, methanol or methanol and water mixture and the unreacted gas included in the reaction mixture are separated. Examples of the separation method include: a condensation separation method in which the outlet gas from the synthesis step is cooled, and the condensed liquid produced by cooling is separated with a gas-liquid separator; and a membrane separation method using a separation membrane, among these the condensation separation method is preferable. In the present embodiment, at least two separation steps (condensation separation steps) using the condensation separation method are provided within the synthesis loop, and one of these steps is preferably the final condensation separation step subsequent to the final synthesis step. The fluid cooled in the condensation separation step is the outlet gas (gaseous reaction mixture) from the synthesis step preceding the condensation separation step, and the outlet gas includes the synthesized methanol. Examples of the method for obtaining the liquid including methanol as a condensed liquid include: an air cooling based on the mutual heat exchange with the synthesis gas supplied to the reactor or an air cooling with an air fin cooler; and a cooling with a coolant such as cooling water or brine. According to the initial temperature before cooling and the target temperature after cooling of the fluid (reaction mixture) being an object to be cooled, the methods for obtaining the condensed liquid are used each alone or in combinations of two or more thereof. Alternatively, it is also possible to combine a technique for obtaining a condensed liquid by utilizing the cooling caused by the expansion of the gas with a pressure reducer which can be used in the method for producing methanol of the present embodiment. In general, the obtained condensed liquid is separated by using a gas-liquid separator (hereinafter, also simply referred to as the "separator"). In combining these coolers (condensers) and separators, a combination of one of these coolers and one of these separators may be adopted, or alternatively, a combination of two or more of these cooler and two or more of these separators may also be adopted. Examples of the combination of two or more of these cooler and two or more of these separators include the combination disclosed in Japanese Patent Application Laid-Open No. 61-257934. More specifically, examples of the above-described combinations include a method in which when the reaction mixture obtained by passing through the synthesis step is cooled, and the reaction product mainly including methanol is condensed and separated, the condenser is divided into two stages, the heat transfer surface temperature of the first-stage condenser is set at a temperature equal to or lower than the dew point of the reaction mixture and equal to or higher than the melting point of the paraffins included in the reaction mixture, and the heat transfer surface temperature of the second-stage condenser is set at 60° C. or lower.

For example, as an embodiment, here is described a case of a production method using a condensation separation method as the separation method in the separation step, and having two synthesis steps and two condensation separation steps. The first condensation separation step is the step of condensing and separating the outlet gas (gaseous reaction mixture) from the first synthesis step, and is arranged subsequently to the first synthesis step. The first condensation separation step extracts methanol from the synthesis loop by separating preferably 35 to 100 mol %, more preferably 35 to 99 mol %, and furthermore preferably 75 to 96 mol % of the methanol included in the outlet gas from the first synthesis step.

In the condensation separation step, the reaction mixture is cooled until a predetermined amount of the condensed liquid including methanol or methanol and water is produced by cooling. For example, when the fluid (reaction mixture) having a methanol partial pressure of 0.69 to 0.88 MPa-G (7.0 to 9.0 kg/cm$^2$-G) is cooled and condensed, the fluid is cooled preferably at 20 to 100° C. and more preferably at 40 to 80° C. In this case, from the viewpoint of improving the methanol yield, in the first condensation separation step, the separation proportion of the methanol included in the outlet gas from the first synthesis step is preferably set at higher than 75 mol %. Moreover, for the reaction control in the subsequent second synthesis step, in the first condensation separation step, the separation proportion of the methanol included in the outlet gas from the first synthesis step is more preferably set at lower than 96 mol %. From the viewpoint of saving the cooling water, the cooling in the first condensation separation step preferably uses only the cooling (air cooling) with an air fin cooler. In this case, the target temperature of the reaction mixture after cooling is preferably 55 to 90° C. from the same viewpoint as described above.

As described above, by providing separation steps between a plurality of synthesis steps, the amounts of water supplied to the reactors are reduced in the synthesis steps subsequent to the separation steps. Consequently, as compared with the case where no separation steps are involved, the sintering of the copper particles considered to be the active sites of the catalyst is suppressed, and hence the effect of extending the catalyst service life is assumed. By providing separation steps between a plurality of synthesis steps, and by using the unreacted gas separated in a separation step as the raw material for the synthesis step subsequent to the separation step, the balance between the reaction amounts in the synthesis steps respectively preceding to and subsequent to the separation step concerned is made satisfactory, and consequently the catalysts can be used more effectively. Moreover, in the separation steps between the plurality of synthesis steps, by supplying to the synthesis step subsequent to one of the separation steps the outlet gas from the synthesis step preceding to the separation step concerned without separating 4 to 25 mol % of the methanol included in the outlet gas, the reaction in the subsequent synthesis step can be controlled and the overheating of the catalyst layer can also be suppressed. In this case, the amount of the condensable gas which is not removed in the separation step is increased.

The outlet gas from the final synthesis step is supplied to the final separation step. The final separation step separates at least a fraction of the methanol included in the outlet gas (gaseous reaction mixture) from the final synthesis step. When the condensation separation is adopted in the final separation step, the outlet gas from the final synthesis step is cooled preferably to 20° C. to 50° C., for example to 45° C., and is separated into the gas phase (the unreacted gas) and the liquid phase with a gas-liquid separator. The reaction products including methanol separated in the respective separation steps in the synthesis loop are taken out as crude methanol.

Because the inert component is accumulated in the synthesis loop, a fraction of the gas is required to be removed as a purge gas to outside the system. The outlet position of the purge gas is only required to be an appropriate position in the synthesis loop. In this case, the flow rate of the purge gas may be appropriately adjusted in such a way that the below described circulation ratio falls within a desired numerical value range. Here, the circulation ratio is defined by the ratio of the molar flow rate of the circulation gas to the molar flow rate of the make-up gas. In the present embodiment, the molar flow rate of the circulation gas is the molar flow rate of the remaining gas obtained by removing the purge gas from the final unreacted gas. The reaction products including methanol separated in the respective separation steps in the synthesis loop are taken out as crude methanol.

From the viewpoint of reducing the amount of the treated gas of the circulator, the outlet of the purge gas in the synthesis loop is positioned preferably at the point of lower pressure in the synthesis loop. In addition, from the viewpoint of the carbon yield, a fraction of the unreacted gas obtained by separating the reaction product from the reaction mixture and discharging the reaction product to the outside of the synthesis loop is preferably divided as a purge gas, and more preferably the outlet of the purge gas is positioned upstream of mixing section of the make-up gas. Furthermore, in each of the separation steps between a plurality of the synthesis steps, by supplying 4 to 25 mol % of methanol included in the outlet gas from the synthesis step in advance of the separation step without separating from the outlet gas, it is possible to control the reaction and prevent the overheat of the catalyst layer in the synthesis step after the separation step. In this case, it is not appropriate to place the circulator downstream of the separator used in the separation step and upstream of the preheater used for heating up placed upstream of the reactor used in the subsequent synthesis step since the condensate may be generated in the circulator.

The circulation ratio in the methanol synthesis process is defined by the ratio of the molar flow rate of the circulation gas to the molar flow rate of the make-up gas. In the present embodiment, the circulation ratio is preferably 0.6 or more and 2.0 or less and more preferably 0.8 or more and 1.5 or less. In comparison of the gas composition of the make-up gas and the gas composition of the circulation gas, the make-up gas is higher in the content proportions of carbon monoxide and carbon dioxide, the raw materials for the methanol synthesis, an exothermic reaction, and hence more tends to generate heat in the catalyst layer. Accordingly, by setting the circulation ratio at 0.6 or more, the overheating of the catalyst mainly due to the make-up gas can be further suppressed through the dilution due to the circulation gas. On the other hand, by setting the circulation ratio at 2.0 or less, the energy efficiency in the whole process is improved. This is because the relative increase of the molar flow rate of the make-up gas allows the molar flow rate of hydrogen or the like, intrinsically needing no cooling, to be reduced, and correspondingly, the load on the cooler can be reduced.

(Pressure Increase Step)

The method for producing methanol of the present embodiment has, in the synthesis loop thereof, at least a pressure increase step. A circulator is used in the pressure increase in the pressure increase step. The method for producing methanol has at least a pressure increase step after the final preheating step and before the final synthesis step. The preheater capable of being used in the final preheating step heats, to a predetermined temperature, the final mixed gas, the gas supplied to the final synthesis step, and is generally preferably an apparatus to performed heat exchange with the final reaction mixture (usually gaseous) obtained by passing through the final synthesis step. In this case, the temperature of the final mixed gas after the preheating is not equal to or higher than the temperature of the final reaction mixture. When an isothermal reactor having an indirect heat exchange mechanism with pressurized boiling water is assumed as the reactor usable in the final synthesis step, because the reactor outlet temperature of the final reaction mixture is asymptotic to the temperature of the pressurized boiling water, the final mixed gas preheated by the preheater is supplied at a temperature lower than the temperature of the pressurized boiling water, and hence the collected amount of the heat of reaction by the pressurized boiling water is decreased. On the other hand, in the present embodiment, by arranging the pressure increase step after the final preheating step and before the final synthesis step, the temperature of the final mixed gas at the reactor inlet can be made close to or higher than the temperature of the pressurized boiling water, the increase of the collected amount of the heat of reaction achieved by the reduction of the circulation ratio is further promoted and a further increase of the collected amount of the heat of reaction is provided. From the viewpoint of effectively and certainly achieving such effects, the pressure ratio between before and after the pressure increase in the pressure increase step preferably exceeds 1.10 and more preferably exceeds 1.20. The upper limit of the pressure ratio is not particularly limited, but is usually approximately 2.00. Moreover, from the viewpoint of achieving effects similar to, but not better than, the above-described effects, the method for producing methanol of the present embodiment may also have another pressure increase step of increasing, before the first synthesis step, the pressure of the first mixed gas having passed through the first preheating step.

(Pressure Reduction Step)

The method for producing methanol of the present embodiment has at least a pressure reduction step in the synthesis loop. The method for producing methanol may have the pressure reduction step after the first synthesis step, and before or after the first separation step. When the first reaction mixture at the outlet of the reactor used in the first synthesis step is used as the heat source for the preheating of the first mixed gas, the method for producing methanol of the present embodiment may have the pressure reduction step after the heat exchange (cooling by the final mixed gas) with the first mixed gas. In addition, the method for producing methanol preferably has the pressure reduction step after the final synthesis step and before the final separation step, and before or after the step of condensing a fraction of the final reaction mixture. Moreover, the method for producing methanol also have the pressure reduction step preferably between after the final separation step and before the first mixing step. When the final reaction mixture at the outlet of the reactor is used as the heat source for the preheating of the final mixed gas, the method for producing methanol of the present embodiment has the pressure reduction step preferably after the heat exchange with the final mixed gas (cooling by the final mixed gas). The inclusion of such a pressure reduction step is preferable from the viewpoint of creating room for collecting energy and reducing the amount of energy used. Examples of the energy collection method include: the energy collection based on power generation using pressure difference; and a pressure transformation energy collection used for the pressure increase of another low-pressure fluid. When the method for producing methanol has the pressure reduction step after the heat exchange of the final reaction mixture with the final mixed gas and before the final separation step, as compared with the case where the method for producing methanol has the pressure reduction step after the final separation step, the amount of the fluid in the pressure reduction step is increased, and hence room for collecting energy can be more created. Moreover, due to the effect of the cooling of the final reaction mixture by the pressure reduction, depending on the target separation temperature, the size of the condenser used for condensing a fraction of the final reaction mixture before the final separation step can be reduced, or the condenser is sometimes made unnecessary. These pressure reduction steps may be arranged either after the passing through the preheater of the reactor outlet gas and before the final separation step, or after the final separation step and before the first mixing step, or according to both of these arrangements.

In the method for producing methanol of the present embodiment, the synthesis loop may have three or more mixing steps, three or more synthesis steps and three or more separation steps. In addition, the synthesis loop may have two or more pressure increase steps and two or more pressure reduction steps. Moreover, when the method for producing methanol uses an isothermal reactor in a synthesis step, and a preheating step of performing heat exchange in a preheater between the mixed gas, the reactor feed gas, and the reactor outlet gas, the synthesis loop preferably has a pressure increase step before one or more synthesis steps, more preferably has a pressure reduction step after the preheating step of the synthesis step, and more preferably has a pressure increase step before each of the synthesis steps and more preferably has a pressure reduction step after the preheating step of each of the synthesis steps. In this paragraph, "before a synthesis step" means, when there is another synthesis step before the synthesis step, the location after the another synthesis step and after the preheating step before the synthesis step; "after the preheating step of a synthesis step" means the location after the passing of the reactor outlet gas of the synthesis step through the preheater, and when there is another synthesis step after the synthesis step, before the preheating step of the another synthesis step. In this way, of the fluids flowing into the preheater, the fluid on the temperature increase side (the reactor feed gas) is decreased in pressure, and the fluid on the temperature decrease side (the reactor outlet gas) is increased in pressure, and hence the heat exchange in the preheater is more promoted.

FIG. 1 is a schematic diagram illustrating an example of the production apparatus used for the method for producing methanol of the present embodiment. The production apparatus is an apparatus for producing methanol, including reactors 23a and 23b each synthesizing methanol from a synthesis gas including hydrogen, carbon monoxide and carbon dioxide, and gas-liquid separators 26a and 26b being the separators separating the unreacted gases from the reaction mixtures obtained in the reactors 23a and 23b, respectively. The apparatus for producing methanol includes a synthesis loop including the two reactors 23a and 23b and the two gas-liquid separators (separators) 26a and 26b, wherein the synthesis loop includes: a first mixing unit (the mixing section of a line 3a with the synthesis loop) obtaining a first mixed gas by mixing the residual gas obtained by removing a purge gas from the second unreacted gas separated from the second reaction mixture in the second gas-liquid separator 26b subsequent to the second reactor 23b with 10 to 90 mol % of the make-up gas including hydrogen, carbon monoxide and carbon dioxide; the first reactor 23a synthesizing methanol from the first mixed gas; a first gas-liquid separator 26a separating the first unreacted gas from the first reaction mixture obtained in the first reactor 23a; the second mixing unit (the mixing section of a line 3b with the synthesis loop) obtaining the second mixed gas by mixing the first unreacted gas and the 10 to 90 mol % of the make-up gas; the second reactor 23b finally synthesizing methanol from the second mixed gas; the second gas-liquid separator 26b separating the second unreacted gas from the second reaction mixture obtained in the second reactor 23b; a circulator 32b increasing the pressure of the second mixed gas after passing through a preheater 22b; and a pressure reducer 34b reducing the pressure of the unreacted gas separated from the second reaction mixture in the gas-liquid separator 26b, and in the reactors 23a and 23b, the reaction temperatures of the catalyst layers in inner tubes 24a and 24b are controlled by the indirect heat exchange with pressurized boiling water. It is to be noted that, although not shown, in place of or in addition to the pressure reducer 34b, there may be included a pressure reducer reducing the pressure of the second reaction mixture after passing through the preheater 22b from the outlet of the reactor 23b. In the present embodiment, the second reactor 23b, the second gas-liquid separator 26b, the second reaction mixture and the second unreacted gas correspond to the final reactor, the final separator, the final reaction mixture and the final unreacted gas, respectively.

The synthesis raw material gas including CO, $CO_2$ and $H_2$, produced by steam-reforming reaction is increased in pressure to a predetermined pressure with a compressor. A predetermined amount of the synthesis raw material gas (make-up gas) increased in pressure is allowed to flow in the line 3a, and then supplied to the synthesis loop. The first mixed gas, obtained by mixing the make-up gas with the circulation gas, in a line 4a is supplied to a preheater 22a. The first mixed gas, the reactor feed gas, is subjected to the heat exchange, in the preheater 22a, with the reactor outlet gas (the first reaction mixture) including the reaction product flowing in a line 7a of the outlet of the reactor 23a, to be preheated to a predetermined temperature, and supplied to the reactor 23a from a line 5a. The residual make-up gas flows in the line 3b.

The reactor 23a has the inner tubes 24a, and the methanol synthesis catalyst including copper and zinc as the essential components is filled in the inner tubes 24a to form the catalyst layer. Methanol is synthesized in the process allowing the first mixed gas supplied from the line 5a into the reactor 23a to pass through the catalyst layer in the inner tubes 24a. The pressure and the temperature of the fluid in the catalyst layer are only required to fall within the pressure range and the temperature range in the above-described methanol synthesis reaction, respectively.

The reactor outlet gas (the first reaction mixture) including methanol, flowing out from the reactor 23a into the line 7a, is cooled in the preheater 22a, and then further cooled by a condenser 25a to a temperature equal to or lower than the dew point of methanol, to promote the condensation of methanol. In the fluid including the condensed methanol, the condensed fraction thereof is extracted in the gas-liquid separator 26a as crude methanol from a line 9a to outside the system, and the residual gas phase fraction thereof flows in the line 8a.

The fraction of the make-up gas, having flowed in the line 3b is mixed with the unreacted gas having flowed from the gas-liquid separator 26a in the line 8a, and then supplied as the second mixed gas, the reactor feed gas, to the preheater 22b from a line 4b. The second mixed gas preheated to a predetermined temperature is supplied from a line 5b to the circulator 32b, increased in pressure to a predetermined reaction pressure, and then supplied to the reactor 23b from a line 6b.

The reactor 23b has the inner tubes 24b, and the methanol synthesis catalyst including copper and zinc as the essential components is filled in the inner tubes 24b to form the catalyst layer. Methanol is synthesized in the process allowing the second mixed gas supplied from the line 6b into the reactor 23b to pass through the catalyst layer in the inner tubes 24b. The pressure and the temperature of the fluid in the catalyst layer are only required to fall within the pressure range and the temperature range in the above-described methanol synthesis reaction, respectively.

The reactor outlet gas (the second reaction mixture) including methanol, flowing out from the reactor 23b into a line 7b, is cooled in the preheater 22b, and then further cooled to a predetermined temperature by a condenser 25b to further condense methanol. In the second reaction mixture including the condensed methanol, the condensed fraction thereof is extracted in the gas-liquid separator 26b as crude methanol from a line 9b to outside the system, and the gas phase fraction thereof (the second unreacted gas) flows in the line 8b. The second unreacted gas flowing in the line 8b is reduced in pressure in the pressure reducer 34b. Subsequently, a fraction of the second unreacted gas of an amount to give a predetermined circulation ratio flows as the circulation gas in a line 16, and mixed with the make-up gas flowing in the line 3a, to be recycled to the reactor 23a. The residual unreacted gas is extracted as the purge gas from the synthesis loop to outside the system from a line 15, in order to remove the inert component accumulating in the synthesis loop.

The cooling operations of the catalyst layers in the reactors 23a and 23b are performed in the process in which the boiler waters from steam drums 33a and 33b are introduced from lines 43a and 43b into the reactors 23a and 23b, respectively, these boiler waters are used as the pressurized boiling waters, and the fluids including the produced steams are collected from lines 44a and 44b in the steam drums 33a and 33b, respectively. The steams produced by the heats of reaction are taken out from the steam drums 33a and 33b to lines 42a and 42b, respectively, and the amounts of water to compensate the amounts of the steams are supplied from lines 41a and 41b to the steam drums 33a and 33b, respectively. The steam taken out from the lines 42a and 42b can be used as the raw material steam necessary for the steam-reforming reaction in the production of the raw material gas from natural gas.

FIG. 3 is a schematic diagram illustrating another example of the production apparatus used for the method for producing methanol of the present embodiment. The difference from the production apparatus shown in FIG. 1 is in that two circulators and two pressure reducers are provided in the synthesis loop. Specifically, one aspect of the difference is that the first mixed gas, the reactor feed gas preheated in the preheater 22a, is supplied from the line 5a to the circulator 32a, and after being increased in pressure by the circulator 32a, supplied to the reactor 23a from a line 6a. Another aspect of the difference is that the first unreacted gas separated in the separator 26a is taken out into the line 8a, then decreased in pressure in a pressure reducer 34a, subsequently mixed with a fraction of the make-up gas from the line 3b, and is supplied from the line 4b to the preheater 22b.

FIG. 4 is a schematic diagram illustrating yet another example of the production apparatus used for the method for producing methanol of the present embodiment. The difference from the production apparatus shown in FIG. 1 is in that three mixing units, three reactors, three gas-liquid separators, three circulators and three compressors are provided. The production apparatus is an apparatus for producing methanol, including the reactors 23a, 23b and 23c each synthesizing methanol from a synthesis gas including hydrogen, carbon monoxide and carbon dioxide; the gas-liquid separators 26a, 26b and 26c being the separators separating the unreacted gases from the reaction mixtures obtained in the reactors 23a, 23b and 23c, respectively; the pressure reducers 34a, 34b and 34c being the apparatuses for reducing the pressures of the unreacted gases obtained in the gas-liquid separators 26a, 26b and 26c, respectively; and circulators 32a, 32b and 32c being the apparatuses for increasing the pressures of the fluids of the mixed gases, the reactor feed gases, after passing through the preheaters 22a, 22b and 22c, respectively. The apparatus for producing methanol includes a synthesis loop including the three reactors 23a, 23b and 23c, and the three gas-liquid separators (separators) 26a, 26b and 26c, wherein the synthesis loop includes: a first mixing unit (the mixing section of the line 3a with the synthesis loop) obtaining a first mixed gas by mixing the residual gas obtained by removing a purge gas from the third unreacted gas separated from the third reaction mixture in a third gas-liquid separator 26c subsequent to the third reactor 23c with 10 to 90 mol % of the make-up gas including hydrogen, carbon monoxide and carbon dioxide; the first reactor 23a synthesizing methanol from the first mixed gas; the first gas-liquid separator 26a separating the first unreacted gas from the first reaction mixture obtained in the first reactor 23a; a second mixing unit (the mixing section of the line 3b with the synthesis loop) obtaining a second mixed gas by mixing the first unreacted gas with 50 to 85 mol % of the make-up gas; the second reactor 23b synthesizing methanol from the second mixed gas; the second gas-liquid separator 26b separating the second unreacted gas from the second reaction mixture obtained in the second reactor 23b; a third mixing unit (the mixing section of a line 3c with the synthesis loop) obtaining a third mixed gas by mixing the second unreacted gas with 5 to 85 mol % of the make-up gas; the third reactor 23c finally synthesizing methanol from the third mixed gas; the third gas-liquid separator 26c separating the third unreacted gas from the third reaction mixture obtained in the third reactor 23c; the circulators 32a, 32b and 32c increasing the pressures of the mixed gases, the reactor feed gases, after passing through the preheater 22a, 22b and 22c, respectively; the pressure reducers 34a, 34b and 34c reducing the pressures of the unreacted gases separated in the gas-liquid separators 26a, 26b and 26c, and in the reactors 23a, 23b and 23c, the reaction temperatures of the catalyst layers in the inner tubes 24a, 24b and 24c are controlled by the indirect heat exchange with pressurized boiling water. It is to be noted that, although not shown, in place of or in addition to the pressure reducers 34a, 34b and 34c, there may be included pressure reducers reducing the pressures of the reaction mixtures after passing through the preheaters 22a, 22b and 22c from the outlets of the reactors 23a, 23b and 23c, respectively. In the present embodiment, the third reactor 23c, the third gas-liquid separator 26c, the third reaction mixture and the third unreacted gas correspond to the final reactor, the final separator, the final reaction mixture and the final unreacted gas, respectively.

The synthesis raw material gas including CO, $CO_2$ and $H_2$, produced by steam-reforming reaction is increased in pressure to a predetermined pressure with the compressor. A predetermined amount of the synthesis raw material gas (make-up gas) increased in pressure is allowed to flow in the line 3a, and then supplied to the synthesis loop. The reactor feed gas (the first mixed gas) in the line 4a, mixed with the make-up gas is supplied to the preheater 22a. The first mixed gas is subjected to the heat exchange, in the preheater 22a, with the reactor outlet gas (the first reaction mixture) including the reaction product flowing in the line 7a of the outlet of the reactor 23a, to be preheated to a predetermined temperature, supplied from the line 5a to the circulator 32a, increased in pressure to a predetermined reaction pressure, and then supplied to the reactor 23a from the line 6a.

The reactor 23a has the inner tubes 24a, and the methanol synthesis catalyst including copper and zinc as the essential components is filled in the inner tubes 24a to form the catalyst layer. Methanol is synthesized in the process allowing the first mixed gas supplied from the line 6a into the reactor 23a to pass through the catalyst layer in the inner tubes 24a. The pressure and the temperature of the fluid in the catalyst layer are only required to fall within the pressure range and the temperature range in the above-described methanol synthesis reaction, respectively.

The outlet gas (the first reaction mixture) including methanol, flowing out from the reactor 23a into the line 7a, is cooled in the preheater 22a, and then further cooled by a condenser 25a to a temperature equal to or lower than the dew point of methanol, to promote the condensation of methanol. In the fluid including the condensed methanol, the condensed fraction thereof is extracted in the gas-liquid separator 26a as crude methanol from a line 9a to outside the system, and the residual gas phase fraction thereof flows in the line 8a. The first unreacted gas taken out into the line 8a is reduced in pressure to a predetermined pressure by the pressure reducer 34a.

The fraction of the make-up gas, having flowed in the line 3b is mixed with the first unreacted gas having flowed from the gas-liquid separator 26a in the line 8a, and then supplied as the reactor feed gas (the second mixed gas) from the line 4b to the preheater 22b. The second mixed gas preheated to a predetermined temperature is supplied from the line 5b to the circulator 32b, increased in pressure to a predetermined reaction pressure, and then supplied to the reactor 23b from the line 6b.

The reactor 23b has the inner tubes 24b, and the methanol synthesis catalyst including copper and zinc as the essential components is filled in the inner tubes 24b to form the catalyst layer. Methanol is synthesized in the process allowing the second mixed gas supplied from the line 6b into the reactor 23b to pass through the catalyst layer in the inner tubes 24b. The pressure and the temperature of the fluid in the catalyst layer are only required to fall within the pressure range and the temperature range in the above-described methanol synthesis reaction, respectively.

The reactor outlet gas (the second reaction mixture) including methanol, flowing out from the reactor 23b into the line 7b, is cooled in the preheater 22b, and then further cooled by a condenser 25b to promote the condensation of methanol. In the fluid including the condensed methanol, the condensed fraction thereof is extracted in the gas-liquid separator 26b as crude methanol from a line 9b to outside the system, and the residual gas phase fraction thereof flows in a line 8b. The second unreacted gas taken out into the line 8b is reduced in pressure to a predetermined pressure by the pressure reducer 34b.

The fraction of the make-up gas, having flowed in the line 3c is mixed with the second unreacted gas having flowed from the gas-liquid separator 26b in the line 8b, and then supplied as the reactor feed gas (the third mixed gas) from a line 4c to the preheater 22c. The third mixed gas preheated to a predetermined temperature is supplied from a line 5c to the circulator 32c, increased in pressure to a predetermined reaction pressure, and then supplied to the reactor 23c from a line 6c.

The reactor 23c has the inner tubes 24c, and the methanol synthesis catalyst including copper and zinc as the essential components is filled in the inner tubes 24c to form the catalyst layer. Methanol is synthesized in the process allowing the third mixed gas supplied from the line 6c into the reactor 23c to pass through the catalyst layer in the inner tubes 24c. The pressure and the temperature of the fluid in the catalyst layer are only required to fall within the pressure range and the temperature range in the above-described methanol synthesis reaction, respectively.

The reactor outlet gas (the third reaction mixture) including methanol, flowing out from the reactor 23c into the line 7c, is cooled in the preheater 22c, and then further cooled to a predetermined temperature by a condenser 25c to further condense methanol. In the fluid including the condensed methanol, the condensed fraction thereof is extracted in the gas-liquid separator 26c as crude methanol from a line 9c to outside the system, and the residual gas phase fraction thereof (the third unreacted gas) flows in the line 8c. The third unreacted gas taken out into the line 8c is reduced in pressure to a predetermined pressure by the pressure reducer 34c.

Of the third unreacted gas flowing in the line 8c, the third unreacted gas of an amount to give a predetermined circulation ratio passes as the circulation gas through the line 16, and mixed with the make-up gas flowing in the line 3a, to be recycled to the reactor 23a. The rest of the third unreacted gas is extracted as the purge gas from the synthesis loop to outside the system from the line 15, in order to remove the inert component accumulating in the synthesis loop.

The cooling operations of the catalyst layers in the reactors 23a, 23b and 23c are performed in the process in which the boiler waters from steam drums 33a, 33b and 33c are introduced from lines 43a, 43b and 43c into the reactors 23a, 23b and 23c, respectively, these boiler waters are used as the pressurized boiling waters, and the fluids including the produced steams are collected from lines 44a, 44b and 44c in the steam drums 33a, 33b and 33c, respectively. The steams produced by the heats of reaction are taken out from the steam drums 33a, 33b and 33c to lines 42a, 42b and 42c, respectively, and the amounts of water to compensate the amounts of the steams are supplied from lines 41a, 41b and 41c to the respective steam drums. The steam taken out from the lines 42a, 42b and 42c can be used as the raw material steam necessary for the steam-reforming reaction in the production of the raw material gas from natural gas.

In the method for producing methanol using the production apparatus, an operation of obtaining a second mixed gas by mixing the first unreacted gas and at least a fraction of 10 to 90 mol % of the make-up gas corresponds to an intermediate mixing step, an operation of synthesizing methanol from the second mixed gas corresponds to an intermediate synthesis step, and an operation of separating the second unreacted gas from the second reaction mixture corresponds to an intermediate separation step.

EXAMPLES

Hereinafter, the present invention is described in more detail by way of Examples and Comparative Examples of the methanol synthesis plant design, but the present invention is not limited to these Examples and Comparative Examples.

The catalyst used in the methanol synthesis was the catalyst (the methanol synthesis catalyst A) prepared by the method described in Example 3 of International Publication No. WO 2011/048976.

Example 1

In Example 1, the production apparatus shown in FIG. 1 was used. The involved conditions were as follows. Specifically, as the raw material gas, the gas produced by the steam-reforming reaction of natural gas was used, and the synthesis of methanol was performed under the condition of a circulation ratio of 1.0. As the catalysts in the reactors 23a and 23b, the methanol synthesis catalyst A was used. The raw material gas was increased in pressure to 8.0 MPa-G with a compressor. Then, 50 mol % of the synthesis raw material gas (make-up gas) increased in pressure was allowed to flow in the line 3a, and was mixed with the circulation gas flowing in the line 16 to obtain the reactor feed gas (the first mixed gas). The first mixed gas having flowed in the line 4a was subjected to the heat exchange in the preheater 22a, with the reactor outlet gas (the first reaction mixture) including the reaction product, flowing in the line 7a of the outlet of the reactor 23a, and thus preheated in such a way that the temperature in the line 5a was 200° C. The rest of the make-up gas, namely, 50 mol % of the make-up gas was allowed to flow in the line 3b. The first mixed gas after the preheating was supplied to the reactor 23a, and the synthesis of methanol was performed (the first synthesis step). In the catalyst layer of the reactor 23a, the pressure of the fluid was 7.8 MPa-G and the temperature was between 200 and 254° C.

The outlet gas (the first reaction mixture) from the first synthesis step was cooled with the condenser 25a to a temperature equal to or lower than the dew point of methanol, namely, 45° C. (total pressure: 7.6 MPa-G), to promote the condensation of methanol. The first unreacted gas separated in the gas-liquid separator 26a was allowed to flow in the line 8a, and mixed with the make-up gas flowing in the line 3b, and thus the reactor feed gas (the second mixed gas) was obtained. The second mixed gas having flowed in the line 4b was subjected to the heat exchange in the preheater 22b with the outlet gas (the second reaction mixture) including the reaction product, flowing in the line 7b of the outlet of the reactor 23b, and thus preheated in such a way that the temperature in the line 5b was 190° C. The second mixed gas flowing in the line 5b was increased in pressure in such a way that the pressure of the line 6b was 9.8 MPa-G in the process of passing through the circulator 32b. Along with the pressure increase, the temperature of the second mixed gas flowing in the line 6b was 230° C. The second mixed gas after the pressure increase was supplied to the reactor 23b, and the synthesis of methanol was performed. In the catalyst layer, the pressure of the fluid was 9.8 MPa-G, and the temperature was between 230 and 265° C. The outlet gas (the second reaction mixture) including methanol, flowing out from the reactor 23b into the line 7b, was cooled in the preheater 22b, and then cooled to 45° C. with the condenser 25b to further condense methanol. The second unreacted gas separated in the gas-liquid separator 26b was allowed to flow in the line 8b, and reduced in pressure in the process of passing through the pressure reducer 34; then, a fraction of the second unreacted gas was taken out as the purge gas from the line 15, and the rest of the second unreacted gas was allowed to be the circulation gas flowing in the line 16. The molar flow rate of the circulation gas flowing in the line 16 was controlled so as to be equal to the molar flow rate of the make-up gas, and consequently, the molar flow rate of the purge gas (the line 15) based on the molar flow rate of the second unreacted gas in the line 8b was 19.4%.

The mass balances are shown in Table 1. The line numbers are the line numbers shown in FIG. 1, and the temperature, the pressure and the material flow rates of the fluid flowing in each of the lines are shown.

TABLE 1

| Line number | Temperature °C. | Pressure MPa-G | Flow rate kg-mol/h | | | | | | | |
|---|---|---|---|---|---|---|---|---|---|---|
| | | | $CO_2$ | CO | $H_2$ | $CH_4$ | $N_2$ | $H_2O$ | $CH_3OH$ | Impurity |
| 3a | 117 | 8.0 | 583 | 1110 | 5386 | 227 | 10 | 8 | 0 | 0 |
| 3b | 117 | 8.0 | 583 | 1110 | 5386 | 227 | 10 | 8 | 0 | 0 |
| 5a | 200 | 7.8 | 768 | 1153 | 17818 | 2043 | 94 | 12 | 78 | 3 |
| 7a | 231 | 7.8 | 293 | 86 | 14260 | 2043 | 94 | 491 | 1614 | 6 |
| 8a | 45 | 7.6 | 287 | 86 | 14244 | 2037 | 94 | 6 | 109 | 4 |
| 9a | 45 | 7.6 | 7 | 0 | 16 | 7 | 0 | 485 | 1504 | 2 |
| 6b | 230 | 9.8 | 870 | 1196 | 19630 | 2264 | 105 | 14 | 109 | 4 |
| 7b | 231 | 9.8 | 237 | 54 | 15449 | 2264 | 104 | 650 | 1876 | 8 |
| 8b | 45 | 9.6 | 230 | 54 | 15426 | 2254 | 104 | 5 | 97 | 4 |
| 9b | 45 | 9.6 | 7 | 0 | 23 | 10 | 0 | 644 | 1780 | 3 |
| 16 | 31 | 7.9 | 185 | 43 | 12432 | 1816 | 84 | 4 | 78 | 3 |

The highest temperature of the catalyst layer in Example 1 was 254° C. in the inner tubes 24a of the reactor 23a, and 265° C. in the inner tubes 24b of the reactor 23b, these temperatures falling within an extremely preferable temperature range as the catalyst use temperature range. In this case, the temperature of the pressurized boiling water, a coolant, was 230° C. The collected heat amount was 89.7 MW, and the motive power of the circulator was 8.8 MW.

The carbon yield in Example 1 is represented by the percentage of the methanol molar flow rate (the sum of the methanol molar flow rate in the line 9a and the methanol molar flow rate in the line 9b) in the crude methanol based on the sum of the CO molar flow rate and the $CO_2$ molar flow rate in the make-up gas (the sum of the CO molar flow rate and the $CO_2$ molar flow rate in the line 3a and the line 3b), and was 97.0% (hereinafter, the carbon yields were calculated in the same manner).

Comparative Example 1

In Comparative Example 1, the production apparatus shown in FIG. 2 was used. Comparative Example 1 is different from Example 1 with respect to the position of the circulator in the synthesis loop. Specifically, the rest of the unreacted gas separated in the gas-liquid separator 26a was taken out in the line 8a, and was increased in pressure after the mixing of the make-up gas from the line 3b and before passing through the preheater 22b. The compositions, the total molar flow rate, the temperatures and pressures of the make-up gases flowing in the line 3a and the line 3b were set to be the same as in Example 1. Comparative Example 1 is based on the technique of Patent Document 2.

The mass balances in Comparative Example 1 are shown in Table 2. The line numbers are the line numbers shown in FIG. 2, and the temperature, the pressure and the material flow rates of the fluid flowing in each of the lines are shown.

TABLE 2

| Line number | Temperature °C. | Pressure MPa-G | Flow rate kg-mol/h | | | | | | | |
|---|---|---|---|---|---|---|---|---|---|---|
| | | | $CO_2$ | CO | $H_2$ | $CH_4$ | $N_2$ | $H_2O$ | $CH_3OH$ | Impurity |
| 3a | 117 | 8.0 | 583 | 1110 | 5386 | 227 | 10 | 8 | 0 | 0 |
| 3b | 117 | 8.0 | 583 | 1110 | 5386 | 227 | 10 | 8 | 0 | 0 |
| 5a | 200 | 7.8 | 778 | 1155 | 17814 | 2037 | 94 | 12 | 78 | 3 |
| 7a | 231 | 7.8 | 299 | 88 | 14243 | 2037 | 94 | 494 | 1618 | 6 |
| 8a | 45 | 7.6 | 292 | 87 | 14228 | 2031 | 94 | 6 | 109 | 4 |
| 9a | 45 | 7.6 | 7 | 0 | 16 | 7 | 0 | 489 | 1509 | 2 |
| 5b | 200 | 9.8 | 875 | 1197 | 19613 | 2258 | 104 | 14 | 109 | 4 |
| 7b | 231 | 9.8 | 249 | 56 | 15454 | 2258 | 104 | 643 | 1869 | 8 |
| 8b | 45 | 9.6 | 242 | 56 | 15431 | 2248 | 104 | 5 | 97 | 4 |
| 9b | 45 | 9.6 | 8 | 0 | 23 | 10 | 0 | 638 | 1772 | 3 |
| 16 | 31 | 7.9 | 195 | 45 | 12428 | 1810 | 84 | 4 | 78 | 3 |

The highest temperature of the catalyst layer in Comparative Example 1 was 254° C. in the inner tubes 24a of the reactor 23a, and 260° C. in the inner tubes 24b of the reactor 23b. In this case, the temperature of the pressurized boiling water, a coolant, was 230° C., the collected heat amount was 81.8 MW and the motive power of the circulator was 6.5 MW.

The carbon yield in Comparative Example 1 was 96.9%.

The difference between Example 1 and Comparative Example 1 is whether a circulator is arranged in advance of the preheater or subsequently to the preheater. In the results of Example 1 having the pressure increase step subsequent to the preheating in a preheater, as compared with the results of Comparative Example 1 performing preheating after pressure increase, although the input energy into the circulator was increased by +2.3 MW, the collected energy in the reactor was increased by +7.9 MW, and hence an energy reduction effect of 5.6 MW was exhibited in total.

Example 2

In Example 2, the production apparatus shown in FIG. 3 was used. The involved conditions were as follows. Specifically, as the raw material gas, the gas produced by the steam-reforming reaction of natural gas was used, and the synthesis of methanol was performed under the condition of the circulation ratio of 1.0. As the catalysts in the reactors 23a and 23b, the methanol synthesis catalyst A was used. The raw material gas was increased in pressure to a pressure of 8.0 MPa-G with a compressor. Then, 50 mol % of the synthesis raw material gas (make-up gas) increased in pressure was allowed to flow in the line 3a, and mixed with the circulation gas flowing in the line 16, to obtain the reactor feed gas (the first mixed gas). The first mixed gas having flowed in the line 4a was subjected to the heat exchange in the preheater 22a with the outlet gas (the first reaction mixture) including the reaction product, flowing in the line 7a of the outlet of the reactor 23a, and thus preheated in such a way that the temperature in the line 5a was 195° C. The first mixed gas flowing in the line 5a was increased in pressure in such a way that the pressure of the line 6a was 9.8 MPa-G in the process of passing through the circulator 32a. Along with the pressure increase, the temperature of the first mixed gas flowing in the line 6a was 230° C. The rest of the make-up gas, namely, 50 mol % of the make-up gas was allowed to flow in the line 3b. The first mixed gas after the pressure increase was supplied to the reactor 23a, and the synthesis of methanol was performed (the first synthesis step). In the catalyst layer, the pressure of the fluid was 9.8 MPa-G, and the temperature was between 230 and 272° C.

The outlet gas (the first reaction mixture) from the first synthesis step was cooled with the condenser 25a to a temperature equal to or lower than the dew point of methanol, namely, 45° C. (total pressure: 9.6 MPa-G), to promote the condensation of methanol. The first unreacted gas separated in the gas-liquid separator 26a was allowed to flow in the line 8a, reduced in pressure in the process of passing through the pressure reducer 34a, and then mixed with the make-up gas flowing in the line 3b, and thus the reactor feed gas (the second mixed gas) was obtained. The second mixed gas having flowed in the line 4b was subjected to the heat exchange in the preheater 22b with the outlet gas (the second reaction mixture) including the reaction product, flowing in the line 7b of the outlet of the reactor 23b, and thus preheated in such a way that the temperature in the line 5b was 195° C. The second mixed gas flowing in the line 5b was increased in pressure in such a way that the pressure of the line 6b was 9.8 MPa-G in the process of passing through the circulator 32b. Along with the pressure increase, the temperature of the second mixed gas flowing in the line 6b was 230° C. The second mixed gas after the pressure increase was supplied to the reactor 23b, and the synthesis of methanol was performed. In the catalyst layer, the pressure of the fluid was 9.8 MPa-G, and the temperature was between 230 and 269° C. The outlet gas (the second reaction mixture) including methanol, flowing out from the reactor 23b into the line 7b, was cooled in the preheater 22b, and then cooled to 45° C. with the condenser 25b to further condense methanol. The second unreacted gas separated in the gas-liquid separator 26b was allowed to flow in the line 8b, and reduced in pressure in the process of passing through the pressure reducer 34; then, a fraction of the second unreacted gas was taken out as the purge gas from the line 15, and the rest of the second unreacted gas was allowed to be the circulation gas flowing in the line 16. The molar flow rate of the circulation gas flowing in the line 16 was controlled so as to be 1.0 times the molar flow rate of the make-up gas, and consequently, the molar flow rate of the purge gas (the line 15) based on the molar flow rate of the second unreacted gas in the line 8b was 19.4%.

The mass balances are shown in Table 3. The line numbers are the line numbers shown in FIG. 3, and the temperature, the pressure and the material flow rates of the fluid flowing in each of the lines are shown.

TABLE 3

| Line number | Temperature ° C. | Pressure MPa-G | Flow rate kg-mol/h | | | | | | | |
|---|---|---|---|---|---|---|---|---|---|---|
| | | | $CO_2$ | CO | $H_2$ | $CH_4$ | $N_2$ | $H_2O$ | $CH_3OH$ | Impurity |
| 3a | 117 | 8.0 | 583 | 1110 | 5386 | 227 | 10 | 8 | 0 | 0 |
| 3b | 117 | 8.0 | 583 | 1110 | 5386 | 227 | 10 | 8 | 0 | 0 |
| 6a | 230 | 9.8 | 725 | 1146 | 17842 | 2069 | 96 | 12 | 78 | 3 |
| 7a | 230 | 9.8 | 178 | 45 | 13998 | 2069 | 96 | 562 | 1720 | 6 |
| 8a | 45 | 9.6 | 173 | 45 | 13977 | 2060 | 96 | 5 | 88 | 4 |
| 9a | 45 | 9.6 | 6 | 0 | 21 | 9 | 0 | 558 | 1632 | 3 |
| 11a | 31 | 7.9 | 173 | 45 | 13977 | 2060 | 96 | 5 | 88 | 4 |
| 6b | 230 | 9.8 | 756 | 1154 | 19363 | 2287 | 106 | 13 | 88 | 4 |
| 7b | 230 | 9.8 | 180 | 46 | 15420 | 2287 | 106 | 591 | 1764 | 7 |
| 8b | 45 | 9.6 | 175 | 46 | 15399 | 2277 | 106 | 5 | 97 | 4 |
| 9b | 45 | 9.6 | 5 | 0 | 22 | 10 | 0 | 586 | 1668 | 3 |
| 16 | 31 | 7.9 | 142 | 37 | 12456 | 1842 | 85 | 4 | 78 | 3 |

The highest temperature of the catalyst layer in Example 2 was 272° C. in the inner tubes 24a of the reactor 23a, and 269° C. in the inner tubes 24b of the reactor 23b, these temperatures falling within a preferable temperature range as the catalyst use temperature range. In this case, the temperature of the pressurized boiling water, a coolant, was 230° C., the collected heat amount was 97.4 MW and the motive power of the circulator was 14.5 MW in total.

The carbon yield in Example 2 was 97.5%.

In the results of Example 2, as compared with the results of Comparative Example 1, although the input energy into the circulator was increased by +8.0 MW, the collected energy in the reactor was increased by +15.6 MW, and hence an energy reduction effect of 7.6 MW was exhibited in total. In addition, when the pressure energy was collected in the pressure reduction operation in the pressure reducer, the energy collection in Comparative Example was 2.6 MW, and the energy collection in Example 2 was 5.0 MW, and hence an energy reduction effect of 10.0 MW was achieved as the sum total of these values.

Example 3

In Example 3, the production apparatus shown in FIG. 4 was used. The involved conditions were as follows. Specifically, as the raw material gas, the gas produced by the steam-reforming reaction of natural gas was used, and the synthesis of methanol was performed under the condition of the circulation ratio of 1.0. As the catalysts in the reactors 23a, 23b and 23c, the methanol synthesis catalyst A was used. The raw material gas was increased in pressure to a pressure of 8.0 MPa-G with a compressor. Then, 30 mol % of the synthesis raw material gas (make-up gas) increased in pressure was allowed to flow in the line 3a, and mixed with the circulation gas flowing in the line 16 to obtain the reactor feed gas (the first mixed gas) The first mixed gas having flowed in the line 4a was subjected to the heat exchange in the preheater 22a with the outlet gas (the first reaction mixture) including the reaction product, flowing in the line 7a of the outlet of the reactor 23a, and thus preheated in such a way that the temperature in the line 5a was 195° C. The first mixed gas flowing in the line 5a was increased in pressure in such a way that the pressure of the line 6a was 9.8 MPa-G in the process of passing through the circulator 32a. Along with the pressure increase, the temperature of the first mixed gas flowing in the line 6a was 230° C. The rest of the make-up gas, namely, 50 mol % of the make-up gas was allowed to flow in the line 3b, and the remaining 20 mol % in the line 3c. The first mixed gas after the pressure increase was supplied to the reactor 23a, and the synthesis of methanol was performed (the first synthesis step). In the catalyst layer of the reactor 23a, the pressure of the fluid was 9.8 MPa-G, and the temperature was between 230 and 264° C.

The outlet gas (the first reaction mixture) from the first synthesis step was cooled with the condenser 25a to a temperature equal to or lower than the dew point of methanol, namely, 80° C. (total pressure: 9.6 MPa-G), to promote the condensation of methanol. The first unreacted gas separated in the gas-liquid separator 26a was allowed to flow in the line 8a, reduced in pressure in the process of passing through the pressure reducer 34a, and then mixed with the make-up gas flowing in the line 3b, and thus the reactor feed gas (the second mixed gas) was obtained. The second mixed gas having flowed in the line 4b was subjected to the heat exchange in the preheater 22b with the outlet gas (the second reaction mixture) including the reaction product, flowing in the line 7b of the outlet of the reactor 23b, and thus preheated in such a way that the temperature in the line 5b was 195° C. The second mixed gas flowing in the line 5b was increased in pressure in such a way that the pressure of the line 6b was 9.8 MPa-G in the process of passing through the circulator 32b. Along with the pressure increase, the temperature of the second mixed gas flowing in the line 6b was 230° C. In the catalyst layer, the pressure of the fluid was 9.8 MPa-G, and the temperature was between 230 and 265° C. The outlet gas (the second reaction mixture) including methanol, flowing out from the reactor 23b into the line 7b, was cooled in the preheater 22b, and then cooled to 45° C. with the condenser 25b to further condense methanol. The second unreacted gas separated in the gas-liquid separator 26b was allowed to flow in the line 8b, reduced in pressure in the process of passing through the pressure reducer 34b, and then mixed with the make-up gas flowing in the line 3c, and thus the reactor feed gas (the third mixed gas) was obtained. The third mixed gas having flowed in the line 4c was subjected to the heat exchange in the preheater 22c with the outlet gas (the third reaction product) including the reaction product, flowing in the line 7c of the outlet of the reactor 23c, and thus preheated in such a way that the temperature in the line 5c was 195° C. The third mixed gas flowing in the line 5c was increased in pressure in such a way that the pressure of the line 6c was 9.8 MPa-G in the process of passing through the circulator 32c. Along with the pressure increase, the temperature of the third mixed gas flowing in the line 6c was 230° C. The third mixed gas after the pressure increase was supplied to the reactor 23c, and the synthesis of methanol was performed. In the catalyst layer, the pressure of the fluid was 9.8 MPa-G, and the temperature was between 230 and 254° C. The outlet gas (the third reaction product) including methanol, flowing out from the reactor 23c into the line 7c, was cooled in the preheater 22c, and then cooled to 45° C. with the condenser 25c to further condense methanol. The third unreacted gas separated in the gas-liquid separator 26c was allowed to flow in the line 8c, and reduced in pressure in the process of passing through the pressure reducer 34c; then, a fraction of the third unreacted gas was taken out as the purge gas from the line 15, and the rest of the third unreacted gas was allowed to be the circulation gas flowing in the line 16. The molar flow rate of the circulation gas flowing in the line 16 was controlled so as to be 1.0 times the molar flow rate of the make-up gas, and consequently, the molar flow rate of the purge gas (the line 15) based on the molar flow rate of the third unreacted gas in the line 8b was 18.5%.

The mass balances are shown in Table 4. The line numbers are the line numbers shown in FIG. 4, and the temperature, the pressure and the material flow rates of the fluid flowing in each of the lines are shown.

TABLE 4

| Line number | Temperature °C. | Pressure MPa-G | Flow rate kg-mol/h | | | | | | | |
|---|---|---|---|---|---|---|---|---|---|---|
| | | | $CO_2$ | CO | $H_2$ | $CH_4$ | $N_2$ | $H_2O$ | $CH_3OH$ | Impurity |
| 3a | 117 | 8.0 | 348 | 662 | 3215 | 136 | 6 | 5 | 0 | 0 |
| 3b | 117 | 8.0 | 580 | 1104 | 5357 | 226 | 10 | 8 | 0 | 0 |
| 3c | 117 | 8.0 | 232 | 442 | 2143 | 90 | 4 | 3 | 0 | 0 |
| 6a | 230 | 9.8 | 384 | 678 | 15647 | 2048 | 94 | 9 | 78 | 3 |
| 7a | 230 | 9.8 | 54 | 22 | 13343 | 2048 | 94 | 342 | 1060 | 5 |
| 8a | 80 | 9.6 | 53 | 22 | 13332 | 2046 | 94 | 25 | 337 | 5 |
| 9a | 80 | 9.6 | 0 | 0 | 11 | 2 | 0 | 317 | 723 | 1 |
| 11a | 68 | 7.9 | 53 | 22 | 13332 | 2046 | 94 | 25 | 337 | 5 |
| 6b | 230 | 9.8 | 633 | 1126 | 18690 | 2272 | 105 | 33 | 337 | 5 |
| 7b | 230 | 9.8 | 168 | 49 | 15142 | 2272 | 105 | 501 | 1872 | 8 |
| 8b | 45 | 9.6 | 163 | 49 | 15119 | 2262 | 104 | 4 | 95 | 4 |
| 9b | 45 | 9.6 | 5 | 0 | 23 | 10 | 0 | 496 | 1778 | 3 |
| 11b | 31 | 7.9 | 163 | 49 | 15119 | 2262 | 104 | 4 | 95 | 4 |

TABLE 4-continued

| Line number | Temperature °C. | Pressure MPa-G | Flow rate kg-mol/h | | | | | | | |
|---|---|---|---|---|---|---|---|---|---|---|
| | | | $CO_2$ | CO | $H_2$ | $CH_4$ | $N_2$ | $H_2O$ | $CH_3OH$ | Impurity |
| 6c | 230 | 9.8 | 395 | 490 | 17262 | 2352 | 109 | 8 | 95 | 4 |
| 7c | 230 | 9.8 | 45 | 19 | 16912 | 2352 | 109 | 359 | 913 | 6 |
| 8c | 45 | 9.6 | 45 | 19 | 16902 | 2347 | 108 | 6 | 95 | 4 |
| 9c | 45 | 9.6 | 1 | 0 | 11 | 5 | 0 | 353 | 818 | 2 |
| 16 | 31 | 7.9 | 36 | 15 | 12432 | 1912 | 88 | 5 | 78 | 3 |

The highest temperature of the catalyst layer in Example 3 was 264° C. in the inner tubes 24a of the reactor 23a, 265° C. in the inner tubes 24b of the reactor 23b, and 254° C. in the inner tubes 24c of the reactor 23c, these temperatures falling within a preferable temperature range as the catalyst use temperature range. In this case, the temperature of the pressurized boiling water, a coolant, was 230° C., the collected heat amount was 97.5 MW and the motive power of the circulator was 20.0 MW in total.

The carbon yield in Example 3 was 98.5%.

In the results of Example 3, as compared with the results of Comparative Example 1, although the input energy into the circulator was increased by +13.5 MW, the collected energy in the reactor was increased by +15.7 MW, and hence an energy reduction effect of 2.2 MW was exhibited in total. Moreover, when the pressure energy was collected in the pressure reduction operation in the pressure reducer, the energy collection in Comparative Example 1 was 2.6 MW, and the energy collection in Example 3 was 7.8 MW, and hence an energy reduction effect of 7.5 MW was achieved as the sum total of these values.

Example 4

In Example 4, the production apparatus shown in FIG. 5 was used. The involved conditions were as follows. Specifically, as the raw material gas, the gas produced by the steam-reforming reaction of natural gas was used, and the synthesis of methanol was performed under the condition of the circulation ratio of 1.0. As the catalysts in the reactors 23a and 23b, the methanol synthesis catalyst A was used. The raw material gas was increased in pressure to a pressure of 8.0 MPa-G with a compressor. Then, 50 mol % of the synthesis raw material gas (make-up gas) increased in pressure was allowed to flow in the line 3a, and mixed with the circulation gas flowing in the line 16 to obtain the reactor feed gas (the first mixed gas). The first mixed gas having flowed in the line 4a was subjected to the heat exchange in the preheater 22a with the reactor outlet gas (the first reaction mixture) including the reaction product, flowing in the line 7a of the outlet of the reactor 23a, and thus preheated in such a way that the temperature in the line 5a was 200° C. The residual make-up gas, namely, 50 mol % of the make-up gas was allowed to flow in the line 3b. The first mixed gas after the preheating was supplied to the reactor 23a, and the synthesis of methanol was performed (the first synthesis step). In the catalyst layer of the reactor 23a, the pressure of the fluid was 7.8 MPa-G, and the temperature was between 200 and 254° C.

The outlet gas (the first reaction mixture) from the first synthesis step was cooled with the condenser 25a to a temperature equal to or lower than the dew point of methanol, namely, 45° C. (total pressure: 7.6 MPa-G), to promote the condensation of methanol. The first unreacted gas separated in the gas-liquid separator 26a was allowed to flow in the line 8a, and mixed with the make-up gas flowing in the line 3b, and thus the reactor feed gas (the second mixed gas) was obtained. The second mixed gas having flowed in the line 4b was subjected to the heat exchange in the preheater 22b with the outlet gas (the second reaction mixture) including the reaction product, flowing in the line 7b of the outlet of the reactor 23b, and thus preheated in such a way that the temperature in the line 5b was 190° C. The second mixed gas flowing in the line 5b was increased in pressure in such a way that the pressure of the line 6b was 9.8 MPa-G in the process of passing through the circulator 32b. Along with the pressure increase, the temperature of the second mixed gas flowing in the line 6b was 230° C. The second mixed gas after the pressure increase was supplied to the reactor 23b, and the synthesis of methanol was performed. In the catalyst layer, the pressure of the fluid was 9.8 MPa-G, and the temperature was between 230 and 264° C. The outlet gas (the second reaction mixture) including methanol, flowing out from the reactor 23b into the line 7b, was cooled in the preheater 22b, then reduced in pressure in the process of passing through the pressure reducer 34, and cooled to 45° C. with the condenser 25b to further condense methanol. The second unreacted gas separated in the gas-liquid separator 26b was allowed to flow in the line 8b; then, a fraction of the second unreacted gas was taken out as the purge gas from the line 15, and the rest of the second unreacted gas was allowed to be the circulation gas flowing in the line 16. The molar flow rate of the circulation gas flowing in the line 16 was controlled so as to be equal to the molar flow rate of the make-up gas, and consequently, the molar flow rate of the purge gas (the line 15) based on the molar flow rate of the unreacted gas in the line 8b was 19.4%.

The mass balances are shown in Table 5. The line numbers are the line numbers shown in FIG. 5, and the temperature, the pressure and the material flow rates of the fluid flowing in each of the lines are shown.

TABLE 5

| Line number | Temperature °C. | Pressure MPa-G | Flow rate kg-mol/h | | | | | | | |
|---|---|---|---|---|---|---|---|---|---|---|
| | | | $CO_2$ | CO | $H_2$ | $CH_4$ | $N_2$ | $H_2O$ | $CH_3OH$ | Impurity |
| 3a | 117 | 8.0 | 583 | 1110 | 5386 | 227 | 10 | 8 | 0 | 0 |
| 3b | 117 | 8.0 | 583 | 1110 | 5386 | 227 | 10 | 8 | 0 | 0 |
| 5a | 200 | 7.8 | 771 | 1153 | 17798 | 2046 | 94 | 13 | 92 | 4 |

TABLE 5-continued

| Line number | Temperature °C. | Pressure MPa-G | Flow rate kg-mol/h | | | | | | | |
|---|---|---|---|---|---|---|---|---|---|---|
| | | | $CO_2$ | CO | $H_2$ | $CH_4$ | $N_2$ | $H_2O$ | $CH_3OH$ | Impurity |
| 7a | 231 | 7.8 | 297 | 88 | 14245 | 2046 | 94 | 490 | 1626 | 7 |
| 8a | 45 | 7.6 | 290 | 88 | 14229 | 2039 | 94 | 6 | 109 | 4 |
| 9a | 45 | 7.6 | 7 | 0 | 16 | 7 | 0 | 485 | 1516 | 3 |
| 6b | 230 | 9.8 | 873 | 1197 | 19614 | 2266 | 104 | 14 | 109 | 4 |
| 7b | 231 | 9.8 | 239 | 54 | 15428 | 2266 | 104 | 651 | 1879 | 8 |
| 8b | 45 | 7.9 | 233 | 54 | 15409 | 2258 | 104 | 6 | 114 | 5 |
| 9b | 45 | 7.9 | 6 | 0 | 19 | 8 | 0 | 645 | 1764 | 3 |
| 16 | 45 | 7.9 | 188 | 44 | 12412 | 1819 | 84 | 5 | 92 | 4 |

The highest temperature of the catalyst layer in Example 4 was 254° C. in the inner tubes 24a of the reactor 23a, and 264° C. in the inner tubes 24b of the reactor 23b, these temperatures falling within an extremely preferable temperature range as the catalyst use temperature range. In this case, the temperature of the pressurized boiling water, a coolant, was 230° C., the collected heat amount was 89.7 MW and the motive power of the circulator was 8.8 MW in total.

The carbon yield of Example 4 was 96.9%.

In Example 4, the load on the condenser 25b was 31.1 MW, and the collected energy was 3.9 MW in the case of the energy collection performed in the pressure reducer 34b. In Example 1, the load on the condenser 25b was 35.1 MW, and accordingly the load on the condenser was able to be reduced in Example 4 than in Example 1, and this was the result leading to the cost reduction of the condenser itself.

Table 6 shows, for each of Examples 1 to 4 and Comparative Example 1, the energy input into the circulator, the energy collected in the pressure reducer and the energy collected in the reactor, and the collected energy in the whole of the apparatus (net collected energy) as a result of the balance of these results.

TABLE 6

| | Energy input into circulator MW | Energy collected in pressure reducer MW | | | Energy collected in reactor MW | Net collected energy MW |
|---|---|---|---|---|---|---|
| Example 1 | 8.8 | — | — | 2.6 | — | — | 89.7 | 83.5 |
| Comparative Example 1 | 6.5 | — | — | 2.6 | — | — | 81.8 | 77.9 |
| Example 2 | 7.0 | 7.5 | — | 2.4 | 2.6 | — | 97.4 | 87.9 |
| Example 3 | 6.0 | 7.3 | 6.6 | 2.6 | 2.6 | 2.6 | 97.5 | 85.4 |
| Example 4 | 8.8 | — | — | 3.9 | — | — | 89.7 | 84.8 |

The present application is based on Japanese Patent Application (Japanese Patent Application No. 2016-077448) filed on Apr. 7, 2016, and the contents thereof are incorporated herein by reference.

INDUSTRIAL APPLICABILITY

According to the method of the present invention, the catalyst layer temperature is appropriately maintained while the circulation ratio is being reduced, at the same time, the carbon yield in the methanol synthesis can be enhanced, the amount of energy used can be reduced (in other words, the amount of the collected energy can be increased), and the reaction can be allowed to proceed more efficiently. Accordingly, the present invention has industrial applicability in the method for producing methanol and the apparatus for producing methanol.

REFERENCE SIGNS LIST

32a, 32b, 32c: circulator; 22a, 22b, 22c: preheater; 23a, 23b, 23c: reactor; 24a, 24b, 24c: inner tubes; 25a, 25b, 25c: condenser; 26a, 26b, 26c: gas-liquid separator; 33a, 33b, 33c: steam drum; 34a, 34b, 34c: pressure reducer

The invention claimed is:

1. A method for producing methanol comprising:
   synthesis steps of synthesizing methanol from a synthesis gas comprising hydrogen, carbon monoxide and carbon dioxide; and
   separation steps of separating an unreacted gas from a reaction mixture obtained by passing through one of the synthesis steps,
   the method comprising a synthesis loop having at least two of the synthesis steps and at least two of the separation steps,
   wherein the synthesis loop comprises:
   a first mixing step of obtaining a first mixed gas by mixing a residual gas, obtained by removing a purge gas from a final unreacted gas separated from a final reaction mixture in a final separation step subsequent to a final synthesis step, with 10 to 90 mol % of a make-up gas comprising hydrogen, carbon monoxide and carbon dioxide;
   a first synthesis step of synthesizing methanol from the first mixed gas;
   a first separation step of separating a first unreacted gas from a first reaction mixture obtained in the first synthesis step;
   a final mixing step of obtaining a final mixed gas by finally mixing the unreacted gas and at least a fraction of 10 to 90 mol % of the make-up gas;
   the final synthesis step of synthesizing methanol from the final mixed gas; and
   the final separation step of separating the final unreacted gas from the final reaction mixture obtained in the final synthesis step, the synthesis loop also comprises:
- a first preheating step of preheating the first mixed gas;
- a final preheating step of preheating the final mixed gas; and
- a pressure increase step of increasing the pressure of the final mixed gas having passed through the final preheating step before the final synthesis step by using a circulator, and in the synthesis loop, a reaction temperature of a catalyst layer is controlled by indirect heat exchange with pressurized boiling water.

2. The method for producing methanol according to claim 1, wherein a heat source for preheating the final mixed gas in the final preheating step is the final reaction mixture.

3. The method for producing methanol according to claim 2, further comprising a final reaction mixture pressure reduction step of reducing the pressure of the final reaction mixture having preheated the final mixed gas before the final separation step.

4. The method for producing methanol according to claim 1, further comprising a final unreacted gas pressure reduction step of reducing the pressure of the final unreacted gas obtained in the final separation step before the first mixing step.

5. The method for producing methanol according to claim 1, further comprising a pressure increase step of increasing the pressure of the first mixed gas having passed through the first preheating step before the first synthesis step.

6. The method for producing methanol according to claim 1, wherein a heat source for preheating the first mixed gas in the first preheating step is the first reaction mixture.

7. The method for producing methanol according to claim 6, further comprising a first reaction mixture pressure reduction step of reducing the pressure of the first reaction mixture having preheated the first mixed gas before the first separation step.

8. The method for producing methanol according to claim 1, further comprising a first unreacted gas pressure reduction step of reducing the pressure of the first unreacted gas obtained in the first separation step.

9. The method for producing methanol according to claim 1, wherein the pressure ratio between before and after the pressure increase in the pressure increase step exceeds 1.10.

10. The method for producing methanol according to claim 1, further comprising an intermediate mixing step of obtaining an intermediate mixed gas by mixing an unreacted gas and at least a fraction of 10 to 90 mol % of the make-up gas subsequently to the first separation step and before the final mixing step; an intermediate synthesis step of synthesizing methanol from the intermediate mixed gas; and an intermediate separation step of separating an intermediate unreacted gas from the intermediate reaction mixture obtained in the intermediate synthesis step.

11. The method for producing methanol according to claim 3, wherein energy is collected in at least one step of the pressure reduction steps.

12. An apparatus for producing methanol comprising: reactors for synthesizing methanol from a synthesis gas comprising hydrogen, carbon monoxide and carbon dioxide; and separators for separating an unreacted gas from a reaction mixture obtained in one of the reactors, the apparatus comprising a synthesis loop comprising at least two of the reactors and at least two of the separators, wherein the synthesis loop comprises: a first mixing unit for obtaining a first mixed gas by mixing a residual gas, obtained by removing a purge gas from a final unreacted gas separated from a final reaction mixture in a final separator subsequent to a final reactor, with 10 to 90 mol % of a make-up gas comprising hydrogen, carbon monoxide and carbon dioxide; a first reactor for synthesizing methanol from the first mixed gas; a first separator for separating a first unreacted gas from a first reaction mixture obtained in the first reactor; a final mixing unit for obtaining a final mixed gas by finally mixing the unreacted gas and at least a fraction of 10 to 90 mol % of the make-up gas; the final reactor for synthesizing methanol from the final mixed gas; and the final separator for separating the final unreacted gas from the final reaction mixture obtained in the final reactor, the synthesis loop also comprises: a first preheater for preheating the first mixed gas; a final preheater for preheating the final mixed gas; and a circulator for increasing the pressure of the final mixed gas preheated by the final preheater before the preheated final mixed gas is supplied to the final reactor, and at least in the final reactor, a reaction temperature of a catalyst layer is controlled by indirect heat exchange with pressurized boiling water.

13. The method for producing methanol according to claim 2, further comprising a final unreacted gas pressure reduction step of reducing the pressure of the final unreacted gas obtained in the final separation step before the first mixing step.

14. The method for producing methanol according to claim 3, further comprising a final unreacted gas pressure reduction step of reducing the pressure of the final unreacted gas obtained in the final separation step before the first mixing step.

15. The method for producing methanol according to claim 2, further comprising a pressure increase step of increasing the pressure of the first mixed gas having passed through the first preheating step before the first synthesis step.

16. The method for producing methanol according to claim 3, further comprising a pressure increase step of increasing the pressure of the first mixed gas having passed through the first preheating step before the first synthesis step.

17. The method for producing methanol according to claim 4, further comprising a pressure increase step of increasing the pressure of the first mixed gas having passed through the first preheating step before the first synthesis step.

18. The method for producing methanol according to claim 2, wherein a heat source for preheating the first mixed gas in the first preheating step is the first reaction mixture.

19. The method for producing methanol according to claim 3, wherein a heat source for preheating the first mixed gas in the first preheating step is the first reaction mixture.

20. The method for producing methanol according to claim 4, wherein a heat source for preheating the first mixed gas in the first preheating step is the first reaction mixture.

* * * * *